United States Patent
Treco et al.

(10) Patent No.: US 9,422,550 B2
(45) Date of Patent: Aug. 23, 2016

(54) PROTEIN AND PEPTIDE LIBRARIES

(75) Inventors: Douglas A. Treco, Arlington, MA (US); Alonso Ricardo, Boston, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 14/236,399

(22) PCT Filed: Jul. 31, 2012

(86) PCT No.: PCT/US2012/048988
§ 371 (c)(1),
(2), (4) Date: Apr. 29, 2014

(87) PCT Pub. No.: WO2013/019794
PCT Pub. Date: Feb. 7, 2013

(65) Prior Publication Data
US 2014/0234898 A1    Aug. 21, 2014

Related U.S. Application Data

(60) Provisional application No. 61/513,819, filed on Aug. 1, 2011.

(51) Int. Cl.
*C40B 50/06* (2006.01)
*A61K 47/48* (2006.01)
*C12N 15/10* (2006.01)
*C40B 40/08* (2006.01)

(52) U.S. Cl.
CPC ...... *C12N 15/1062* (2013.01); *A61K 47/48092* (2013.01); *A61K 47/48246* (2013.01); *C40B 40/08* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 2002/0031762 A1* | 3/2002 | Merryman et al. | 435/6 |
| 2003/0235852 A1* | 12/2003 | Roberts et al. | 435/6 |
| 2004/0229270 A1 | 11/2004 | Williams | |
| 2004/0229271 A1 | 11/2004 | Williams | |
| 2005/0089913 A1 | 4/2005 | Williams | |
| 2007/0015181 A1 | 1/2007 | Williams | |

OTHER PUBLICATIONS

Graber et al., Reliable semi-synthesis of hydrolysis-resistant 3'-peptidyl-tRNA conjugates containing genuine tRNA modifications; NAR, vol. 38, No. 19, pp. 6796-6802, 2010.*
Josephson et al., MRNA display: from basic principles to macrocylcle drug discovery; Drug Discovery Today; vol. 19, No. 4, 2014.*
Buchini et al., Recent improvements in antigene technology, Curr Opin Chem Biol. vol. 7, pp. 717-726, 2003.*
International Search Report and Written Opinion mailed Nov. 15, 2012 in International Patent Application No. PCT/US2012/048988, 6 pgs.
Communication mailed May 21, 2015 in corresponding European Application No. 12820566.3, 6 pgs.
European Search Report mailed Mar. 26, 2015 in corresponding EP application No. 12820566.3, 3 pgs.

* cited by examiner

*Primary Examiner* — Addison D Ault
(74) *Attorney, Agent, or Firm* — Fish & Richardson P.C.

(57) ABSTRACT

Provided herein are, inter alia, methods for linking an mRNA molecule to a polypeptide (e.g., a peptide or a protein) by linking the mRNA molecule to a linking amino acid in the polypeptide, or by linking the mRNA molecule to a linking tRNA to which the polypeptide is attached, via reactions not catalyzed by the ribosome, and methods for making polypeptide libraries. Also provided are mRNA-protein complexes and mRNA-tRNA-protein complexes, libraries containing these complexes, and methods of using these complexes.

3 Claims, 17 Drawing Sheets

(vi)

(vii)

R: CH₃; CH₂NHAc; CH₂OH; COOH (viii)

(ix)

1. X = OH    Y = NH₂
2. X = NH₂   Y = OH
3. X = H     Y = NH₂
4. X = NH₂   Y = H

US 9,422,550 B2

PROTEIN AND PEPTIDE LIBRARIES

CROSS-REFERENCE TO RELATED APPLICATIONS

This application is a U.S. National Phase Application under 35 U.S.C. §371 of International Patent Application No. PCT/US2012/048988, filed on Jul. 31, 2012, which claims the benefit of U.S. Provisional Patent Application Ser. No. 61/513,819, filed on Aug. 1, 2011. The entire contents of the foregoing are hereby incorporated by reference.

TECHNICAL FIELD

This invention relates, inter alia, to compositions and methods for generating and using libraries of protein and peptide molecules.

BACKGROUND

Polypeptides can adopt three-dimensional structures that are capable of binding to other biological molecules with very high affinity and specificity. A library of random polypeptide sequences can be populated by molecules with a wide variety of three-dimensional structures. In order to isolate a polypeptide with a conformation that interacts with a specific target protein, individual sequences from the library can be prepared and tested or screened for their affinity to the target. However, for very large libraries (>$10^6$ members), the screening of individual sequences for binding affinity is not feasible. To overcome this limitation, a number of techniques have been developed to select novel polypeptides from extremely large, complex mixtures by virtue of their binding affinity to a target.

The ribosome contains two sites that are critical for the function of aminoacylated tRNAs in protein synthesis: the peptidyl transferase center and the decoding site region. The mRNA display strategy developed by Szostak et al. (e.g., U.S. Pat. No. 6,258,558; and Roberts, R. W. and Szostak, J. W. (1997). Proc. Natl. Acad. Sci. USA 94:12297-12302) exploits the catalytic activity of the peptidyl transferase center to link a 3'-puromycin derivatized mRNA to its encoded peptide by creating a peptide bond between the two.

An mRNA can also be linked to a tRNA at the decoding center. This can be achieved through the use of naturally-occurring or artificially-introduced crosslinkers. One naturally-occurring photochemical crosslinker is the well-known Y-base present near (within a few angstroms of) the anticodon of certain tRNAs (see, e.g., U.S. Pat. Nos. 5,843,701; 6,194,550; and 6,440,695). Others (e.g., U.S. Pat. Nos. 6,962,781; 7,351,812; 7,410,761; and 7,488,600) have described combinations wherein a photo-activatable group on one nucleic acid can react with a reactive group on a second nucleic acid.

SUMMARY

Provided herein are functionalized mRNA molecules, functionalized tRNA molecules, mRNA-polypeptide complexes, mRNA-tRNA-polypeptide complexes, and methods for preparing and using mRNA display libraries.

In one aspect of the invention a linking tRNA is crosslinked to an mRNA while the individual elements are engaged with a ribosome. The crosslinking is based on introducing a specific modified nucleoside at a specific position in the mRNA or the linking tRNA. By design, when the anticodon of the linking tRNA forms three base pairs with a codon containing the modified nucleoside of the mRNA, a chemical reaction can either occur spontaneously or be induced to occur by addition of certain chemicals or, in some cases, by exposure to light. Alternatively, the modified nucleoside can be on the linking tRNA. Thus, the crosslinking can occur between a modified "activated" nucleoside on the mRNA and a "reactive" nucleoside within or near the anticodon of the linking tRNA, or between a modified activated nucleoside within or near the anticodon of the linking tRNA and a reactive nucleoside within or near a complementary (or "cognate") codon of the mRNA. In either case, the pairing of the anticodon of the linking tRNA and the complementary codon in the mRNA results in crosslinking the tRNA to the mRNA. The invention further requires that the growing polypeptide chain remain covalently linked to the linking tRNA, and methods for accomplishing such are described. If the polypeptide is covalently attached to the tRNA, and the tRNA becomes crosslinked to the mRNA, then the polypeptide is effectively bound covalently to the mRNA, forming an mRNA-tRNA-polypeptide complex. In some embodiments, the mRNA becomes crosslinked to an amino acid in the polypeptide, forming an mRNA-polypeptide complex. In any of the methods described herein, the polypeptide can be viewed as being "displayed" on the mRNA. Libraries of such polypeptides linked to mRNA are known as mRNA display libraries.

In one aspect, provided herein are methods for linking an mRNA molecule to a polypeptide, these methods including: (a) providing an mRNA molecule containing a crosslinker, wherein the crosslinker is an alkylated, modified, or activated nucleoside; (b) providing a translation system containing a linking aminoacyl-tRNA containing an amino acid residue linked to a linking tRNA by a covalent bond, wherein the linking tRNA contains an anticodon containing a reactive nucleoside that is reactive with the crosslinker; (c) translating the mRNA molecule in the translation system to produce a polypeptide into which the amino acid residue, still linked to the tRNA, is incorporated; and (d) during or after step (c), crosslinking the reactive nucleoside of the anticodon to the crosslinker of the mRNA molecule, thereby linking the mRNA molecule to the polypeptide through the linking tRNA.

In another aspect, provided herein are methods for linking an mRNA molecule to a polypeptide, these methods including: (a) providing an mRNA molecule containing a reactive nucleoside that is reactive with a crosslinker, wherein the crosslinker is an alkylated nucleoside; (b) providing a translation system comprising a linking aminoacyl-tRNA containing an amino acid residue linked to a linking tRNA by a covalent bond, wherein the linking tRNA contains an anticodon containing a crosslinker that is an alkylated nucleoside; (c) translating the mRNA molecule in the translation system to produce a polypeptide into which the amino acid residue, still linked to the linking tRNA, is incorporated; and (d) during or after step (c), crosslinking the reactive nucleoside of the mRNA molecule to the crosslinker of the anticodon of the linking tRNA, thereby linking the mRNA molecule to the polypeptide through the linking tRNA.

The alkylated nucleoside can be an alkylated guanosine. For example, the alkylated guanosine can be an N-7 alkylated guanosine. In some cases, the N-7 alkylated guanosine contains N-(2-acetamidophenyl)-2-bromoacetamide at the N-7 position of the nucleoside. The N-7 alkylated guanosine can also contain one of the following at the N-7 position: (i) N-(3-acetamidophenyl)-2-bromoacetamide; (ii) N-(4-acetamidophenyl)-2-bromoacetamide; (iii) N-((2-acetamidomethyl)benzyl)-2-bromoacetamide; (iv) N-((3-acetamidomethyl)benzyl)-2-bromoacetamide; (v) N-((4-acetamidomethyl)benzyl)-2-bromoacetamide; (vi) (Z/E)-N-

(4-acetamidobut-2-enyl)-2-bromoacetamide; or (vii) (Z/E)-N-(2-acetamidovinyl)-2-bromoacetamide. Reactive nucleosides that are reactive with an alkylated guanosine include 2-thiouridine and 4-thiouridine.

The alkylated nucleoside can also be an S-4-alkylated thiouridine. Guanosine, for example, is a reactive nucleoside that can react (e.g., crosslink) with an S-4-alkylated thiouridine. In some embodiments, the S-4 alkylated thiouridine contains N-(2-acetamidophenyl)-2-bromoacetamide at the S-4 position of the nucleoside. In some embodiments, the S-4 alkylated thiouridine contains one of the following at the S-4 position: (i) N-(3-acetamidophenyl)-2-bromoacetamide; (ii) N-(4-acetamidophenyl)-2-bromoacetamide; (iii) N-((2-acetamidomethyl)benzyl)-2-bromoacetamide; (iv) N-((3-acetamidomethyl)benzyl)-2-bromoacetamide; (v) N-((4-acetamidomethyl)benzyl)-2-bromoacetamide; (vi) (Z/E)-N-(4-acetamidobut-2-enyl)-2-bromoacetamide; or (vii) (Z/E)-N-(2-acetamidovinyl)-2-bromoacetamide.

In another aspect, described herein are methods for linking an mRNA molecule to a polypeptide, these methods including: (a) providing an mRNA molecule containing a crosslinker, wherein the crosslinker is a 4-oxo-2-pentenal moiety attached to a nucleoside; (b) providing a translation system containing a linking aminoacyl-tRNA containing an amino acid residue linked to a linking tRNA by a covalent bond, wherein the linking tRNA contains a reactive nucleoside that is reactive with the crosslinker; (c) translating the mRNA molecule in the translation system to produce a polypeptide into which the amino acid residue, still linked to the linking tRNA, is incorporated; and (d) during or after step (c), crosslinking the reactive nucleoside of the linking tRNA with the crosslinker of the mRNA molecule, thereby linking the mRNA molecule to the polypeptide through the linking tRNA.

In another aspect, provided herein are methods for linking an mRNA molecule to a polypeptide, these methods including: (a) providing an mRNA molecule containing a reactive nucleoside that is reactive with a crosslinker, wherein the crosslinker is a 4-oxo-2-pentenal moiety attached to a nucleoside; (b) providing a translation system containing a linking aminoacyl-tRNA containing an amino acid residue linked to a linking tRNA by a covalent bond, wherein the linking tRNA contains a crosslinker that is a 4-oxo-2-pentenal moiety attached to a nucleoside; (c) translating the mRNA molecule in the translation system to produce a polypeptide into which the amino acid residue, still linked to the linking tRNA, is incorporated; and (d) during or after step (c), crosslinking the reactive nucleoside of the mRNA molecule with the crosslinker of the linking tRNA, thereby linking the mRNA molecule to the polypeptide through the linking tRNA. In some embodiments, the crosslinker may be within or near the anticodon on the linking tRNA and the reactive nucleoside is in or near the complementary codon on the mRNA. In some embodiments, the reactive nucleoside may be within or near the anticodon on the linking tRNA and the crosslinker is in or near the complementary codon on the mRNA.

In yet another aspect, provided herein are methods for linking an mRNA molecule to a polypeptide, these methods including: (a) providing an mRNA molecule containing a nucleoside with a furan moiety attached; (b) providing a translation system containing a linking aminoacyl-tRNA containing an amino acid residue linked to a linking tRNA by a covalent bond, wherein the linking tRNA contains a reactive nucleoside that is reactive with a crosslinker, wherein the crosslinker is a 4-oxo-2-pentenal moiety; (c) translating the mRNA molecule in the translation system to produce a polypeptide into which the amino acid residue, still linked to the linking tRNA, is incorporated; and (d) during or after step (c), adding an oxidizing agent to oxidize the furan moiety to generate a 4-oxo-2-pentenal moiety, and crosslinking the reactive nucleoside of the linking tRNA with the 4-oxo-2-pentenal moiety of the mRNA molecule, thereby linking the mRNA molecule to the polypeptide through the linking tRNA. Alternatively, the furan moiety may be within or near the anticodon on the linking tRNA and the reactive nucleoside is within or near the complementary codon on the mRNA.

In another aspect, provided herein are methods for linking an mRNA molecule to a polypeptide, these methods including: (a) providing an mRNA molecule containing a reactive nucleoside that is reactive with a crosslinker, wherein the crosslinker is a 4-oxo-2-pentenal moiety; (b) providing a translation system containing a linking aminoacyl-tRNA containing an amino acid residue linked to a linking tRNA by a covalent bond, wherein the linking tRNA contains a nucleoside with a furan moiety attached; (c) translating the mRNA molecule in the translation system to produce a polypeptide into which the amino acid residue, still linked to the linking tRNA, is incorporated; and (d) during or after step (c), adding an oxidizing agent to oxidize the furan moiety to generate a 4-oxo-2-pentenal moiety, and crosslinking the reactive nucleoside of the mRNA with the 4-oxo-2-pentenal moiety of the linking tRNA, thereby linking the mRNA molecule to the polypeptide through the linking tRNA. In some embodiments, the nucleoside with a furan moiety attached may be within or near the anticodon on the linking tRNA and the reactive nucleoside is within or near the complementary codon on the mRNA. In some embodiments, the reactive nucleoside may be within or near the anticodon on the linking tRNA and the nucleoside with a furan moiety attached is within or near the complementary codon on the mRNA.

In the methods described herein, the 4-oxo-2-pentenal moiety on the mRNA or the linking tRNA can be generated by (i) reacting an mRNA or linking tRNA molecule containing a 2'-amino nucleoside with an N-hydroxysuccinimide ester of a carboxyalkyl furan to generate an mRNA or tRNA product, and (ii) then treating the mRNA or tRNA product with an oxidizing agent. In some embodiments, the carboxyalkyl furan is 2-(furan-3-yl) acetic acid, 3-(furan-3-yl) propanoic acid, or 4-(furan-3-yl) butanoic acid. Oxidizing agents can include N-bromosuccinimide, meta-chloro peroxybenzoic acid, methylene blue, molecular oxygen, bromine, and ultraviolet light. In some embodiments, the oxidizing agent is added during step (c).

Also provided are methods for linking an mRNA molecule to a polypeptide, these methods including: (a) providing an mRNA molecule containing a crosslinker, wherein the crosslinker is an electrophilic nucleoside that reacts with a nucleophilic nucleoside partner via hybridization-triggered alkylation; (b) providing a translation system containing a linking aminoacyl-tRNA containing an amino acid residue covalently linked to a linking tRNA by a covalent bond, wherein the linking tRNA contains an anticodon containing a nucleophilic nucleoside partner; (c) translating the mRNA molecule in the translation system to produce a polypeptide into which the amino acid residue, still linked to the linking tRNA, is incorporated; and (d) during or after step (c), crosslinking the crosslinker of the mRNA molecule to the nucleophilic nucleoside partner of the linking tRNA, thereby linking the mRNA molecule to the polypeptide through the linking tRNA. Alternatively, the electrophilic nucleoside may be within or near the anticodon on the linking tRNA and the reactive nucleoside is within or near the complementary codon on the mRNA.

In another aspect, provided herein are methods for linking an mRNA molecule to a polypeptide, these methods including: (a) providing an mRNA molecule containing at a nucleophilic nucleoside partner; (b) providing a translation system containing a linking aminoacyl-tRNA containing an amino acid residue linked to a linking tRNA by a covalent bond, wherein the linking tRNA contains an anticodon containing a crosslinker, wherein the crosslinker is an electrophilic nucleoside that reacts with a nucleophilic partner via hybridization-triggered alkylation; (c) translating the mRNA molecule in the translation system to produce a polypeptide into which the amino acid residue, still linked to the linking tRNA, is incorporated; and (d) during or after step (c), crosslinking the crosslinker of the linking tRNA to the nucleophilic nucleoside partner of the mRNA molecule, thereby linking the mRNA molecule to the polypeptide through the linking tRNA. In some embodiments, the crosslinker may be within or near the anticodon on the linking tRNA and the reactive nucleoside is within or near the complementary codon on the mRNA. In some embodiments, the reactive nucleoside may be within or near the anticodon on the linking tRNA and the crosslinker is within or near the complementary codon on the mRNA.

The electrophilic nucleoside and its nucleophilic nucleoside partner can be (i) 2-amino-6-vinylpurine and cytosine; (ii) 2-amino-6-vinylpurine and 4-thiouridine; (iii) 2-alpha-halomethyl adenosine and 2-thiouridine; (iv) 8-alpha-halomethyl purine and 4-thiouridine; (v) 2,8-alpha-halomethyl purine and 4-thiouridine; (vi) 5-methyl-$N^4,N^4$-ethanocytosine and cytosine; (vii) 2-amino-6-(1-ethylsulfinyl)vinyl purine nucleoside and cytosine; (viii) 4-amino-6-oxo-2-vinylpyrimidine nucleoside and uridine; and (ix) 4-amino-6-oxo-2-vinylpyrimidine-ethyl-C-nucleoside and uridine.

In another aspect, provided herein are methods for linking an mRNA molecule to a polypeptide, these methods including: (a) providing an mRNA molecule containing a first member of a complementary crosslinker pair; (b) providing a translation system containing a linking aminoacyl-tRNA containing an amino acid residue linked to a linking tRNA by a covalent bond, wherein the linking tRNA contains an anticodon containing a second member of the complementary crosslinker pair, wherein the complementary crosslinker pair is selected from the following pairs: (i) 2-thiouridine and an adenosine containing an olefin substitution at the 2-position of the purine ring, (ii) 4-thiouridine and 2-amino-6 vinylpurine, and (iii) 4-thiouridine and an adenosine containing a vinyl substituent at the 8-position of the ring; (c) translating the mRNA molecule in the translation system to produce a polypeptide into which the amino acid residue, still linked to the linking tRNA, is incorporated; and (d) during or after step (c), crosslinking the first and second members of the complementary crosslinker pair, thereby linking the mRNA molecule to the polypeptide through the linking tRNA. In this aspect of the invention, it is not critical which member of the crosslinking pair is present on the mRNA and which is present on the linking tRNA.

Crosslinking of the first and second members of the complementary crosslinker pair can be carried out by adding one or more of the following agents: (a) iodine, (b) NBS, (c) ethanethiol and ultraviolet light, (d) bromine, and (e) meta-chloro peroxybenzoic acid.

Generally, in the methods described herein, when the crosslinker (e.g., any of the crosslinkers described herein), reactive nucleoside, nucleoside with a furan moiety attached, nucleophilic nucleoside partner, or first member of the complementary crosslinker pair is located on the mRNA, it is positioned in, or within 3 nucleotides, of an in-frame stop codon on the mRNA molecule. In any of the embodiments described herein, the linking tRNA can be a suppressor tRNA. If the crosslinker (e.g., any of the crosslinkers described herein), reactive nucleoside, nucleoside with a furan moiety attached, nucleophilic nucleoside partner, or first member of the crosslinker pair is on the linking tRNA, then the anticodon in the linking tRNA may correspond to a nonsense or stop codon, as in the case when the linking tRNA corresponds to a suppressor tRNA, or it may correspond to a sense codon, as in the case when the linking tRNA corresponds to an elongator tRNA. Often, the sense codon corresponding to the anticodon in the linking tRNA is followed by one or more stop codons. In some embodiments, the mRNA or linking tRNA molecule comprises one, two or three of the crosslinkers, reactive nucleosides, nucleosides with a furan moiety attached, nucleophilic nucleoside partners, or first members of the complementary crosslinker pair. A purified in vitro translation system is used to translate the mRNA molecule in some cases.

In a further aspect, provided herein are mRNA-tRNA-polypeptide complexes that contain an mRNA covalently linked to a tRNA that is covalently linked to an amino acid in a polypeptide, wherein the mRNA is linked to the tRNA via a bridging group selected from the group of: N-7 alkylpurine, oxadiazabicyclo[3.3.0]octaimine, 4-aminoalkylpyrimidine, 4-thioalkylpyrimidine, 2-thioalkylpyrimidine, 2-aminoalkylpyrimidine, 4-alkyloxypyrimidine, an ether, a thioether, and a secondary amine. Also provided herein are libraries containing a plurality of these mRNA-tRNA-polypeptide complexes, the plurality containing mRNA-tRNA-polypeptide complexes that differ from one another, e.g., wherein the mRNA of each mRNA-tRNA-polypeptide complex encodes a different polypeptide. Also provided herein are methods of screening for a polypeptide that interacts with a target, these methods including: (a) providing any of the mRNA-tRNA-polypeptide libraries described herein; (b) contacting the mRNA-tRNA-polypeptide library with the target; and (c) selecting an mRNA-tRNA-polypeptide complex containing a polypeptide that interacts with the target.

Whereas the preceding methods for linking an mRNA to a polypeptide make use of a linking tRNA and crosslinking at the decoding site of the ribosome, other methods do not utilize a linking tRNA. In these methods, a chemical or photochemical reaction in the vicinity of the peptidyl transfer center of the ribosome serves to covalently crosslink an mRNA to the polypeptide it encodes. In one aspect, provided herein are functionalized RNAs comprising an mRNA containing a coding region and, at the 3' end of the mRNA, a 3' substituent containing a linking moiety selected from the group of (i) a derivative of a ribo adenosine comprising a first member of a reactive pair at its 2' or 3' position, (ii) a derivative of a deoxyribo adenosine containing a first member of a reactive pair at its 3' position, and (iii) a derivative of puromycin containing a first member of a reactive pair, wherein the linking moiety is not capable of participating in ribosome-catalyzed peptide bond formation.

The functionalized RNAs can each include a linking moiety selected from the group of: a) a derivative of 2'-deoxy-2'-amino-adenosine in which the first member of the reactive pair is attached via an amide bond; b) a derivative of 3'-deoxy-3'-amino-adenosine in which the first member of the reactive pair is attached via an amide bond; c) a derivative of 2'-amino-2'-3'-dideoxy-adenosine in which the first member of the reactive pair is attached via an amide bond; d) a derivative of 3'-amino-2'-3'-dideoxy-adenosine in which the first member of the reactive pair is attached via an amide bond; e) a derivative of puromycin in which the first member of the reactive pair is attached via an amide bond; and f) a derivative of 3'-amino-3'-deoxy-$N^6,N^6$-dimethyladenosine in which the first member of the reactive pair is attached via an amide bond.

In some embodiments, the reactive pair is selected from the group of: (a) an azide and an alkyne; (b) an alkene and a thiol or an amine; (c) a tetrazine and a trans-cyclooctane, a cyclopropene, a bicyclo[2.2.1]hept-2-ene or a norbornene; (d) an α-halo-benzyl and a thiol or an amine; (e) an α-halo-carbonyl and a thiol or an amine; and (f) a photocrosslinker and a moiety that reacts with the photocrosslinker. In some embodiments, the photocrosslinker is selected from the group of (a) psoralen (b) phenyl-azide derivatives; (c) phenyl-diazirine derivatives; (d) benzophenone, and (e) alkyl azides.

In some embodiments, the linking moiety of the functionalized RNA is immediately preceded by a CC, CdC, or dCdC sequence.

In some embodiments, one of the last three codons of the coding region of the functionalized RNAs encodes a linking amino acid that contains a second member of the reactive pair. In some embodiments, the last codon of the coding region is a stop codon that is recognized by an aminoacylated suppressor tRNA containing a linking amino acid that contains a second member of the reactive pair. In some embodiments, the linking moiety can be separated from the last codon of the coding region by at least 30 nucleotides of RNA.

In some embodiments, the 3' substituent of the functionalized RNAs can contain a pause moiety between the coding region and the linking moiety. In some embodiments, the pause moiety contains a nucleic acid other than RNA. In some embodiments, the pause moiety contains DNA, LNA, TNA, GNA, PNA, PEG, or peptide. Also provided herein are libraries containing a plurality of functionalized RNAs described herein. In some embodiments, the mRNA of each functionalized RNA of the plurality encodes a different polypeptide.

In another aspect, described herein are mRNA-polypeptide complexes containing a functionalized RNA containing an mRNA, wherein the functionalized RNA is covalently linked via a bridging group to a linking amino acid of a polypeptide, wherein the mRNA encodes the polypeptide and contains a codon encoding the linking amino acid, and wherein the bridging group contains triazole, thioether, secondary amine, pyridazine, 3,4-diazanorcaradiene, benzylthioether, or benzylamine. Also provided are libraries containing a plurality of these mRNA-polypeptide complexes, wherein the plurality contains different mRNA-polypeptide complexes.

In one aspect, provided herein are translation systems containing: (a) a library containing a plurality of functionalized RNAs; and (b) an aminoacylated tRNA containing the linking amino acid. The linking amino acid can be selected from the group of (a) L-azidoalanine; (b) L-azidohomoalanine; (c) L-azidonorvaline; (d) 4-ethynyl-L-phenylalanine; (e) L-homopropargylglycine; (f) L-propynylglycine; (g) cysteine; and (h) lysine. In some embodiments, the aminoacylated tRNA is an aminoacylated suppressor tRNA. In some embodiments, the translation system is a purified translation system.

In one aspect, included herein are methods for linking an mRNA to a polypeptide. The methods including: (a) providing a functionalized RNA described herein; (b) providing a translation system containing an aminoacylated tRNA containing a linking amino acid; (c) translating the mRNA of the functionalized RNA to produce a polypeptide into which the linking amino acid is incorporated; and (d) crosslinking the linking moiety to the linking amino acid, thereby linking the mRNA of the functionalized RNA to the polypeptide. The crosslinking step can be carried out by adding (a) copper, (b) UV light and ethanothiol or beta-mercaptoenthanol, (c) aqueous iodine or bromine, or (d) UV light.

In one aspect, methods of generating a library of mRNA-polypeptide complexes are provided. These methods include: (a) providing a library of functionalized RNAs (a library of functionalized RNAs as described herein); (b) providing a translation system containing an aminoacylated tRNA containing the linking amino acid; (c) translating the mRNAs of the plurality of functionalized RNAs to produce a plurality of diverse polypeptides into each of which the linking amino acid is incorporated; and (d) crosslinking the linking moiety of each functionalized RNA to the linking amino acid incorporated into the polypeptide translated from that functionalized RNA, thereby linking each mRNA of the plurality of functionalized RNAs to the polypeptide it encodes and generating a library of mRNA-polypeptide complexes.

In another aspect, provided herein are methods of screening for a polypeptide that interacts with a target, these methods including: (a) providing a library of the mRNA-polypeptide complexes described herein; (b) contacting the library with the target; and (c) selecting an mRNA-polypeptide complex containing a polypeptide that interacts with the target.

The details of a number of embodiments are set forth in the accompanying drawings and the description below. Other features, objects, and advantages of the disclosed compositions and methods will be apparent from the description and drawings, and from the claims.

The diagram shows the ribosome during translation with the peptidyl-tRNA and aa-tRNA shown prior to the peptide transferase reaction (the aa-tRNA will be the C-terminal amino acid of the peptide) (left). The inset in the diagram shows the triplet codon-anticodon pairing, with the central, reactive base on the mRNA. The diagram shows that the growing peptide chain is transferred to the terminal aa-tRNA, and the new peptidyl-tRNA and the mRNA translocates within the ribosome (immediately to the right of the inset). The right part of the diagram shows that after removal of the ribosome, the peptide and mRNA remain attached due to the bases in the codon (1) and anticodon, and the unstable link between the peptide and the tRNA (2).

Figure 2:
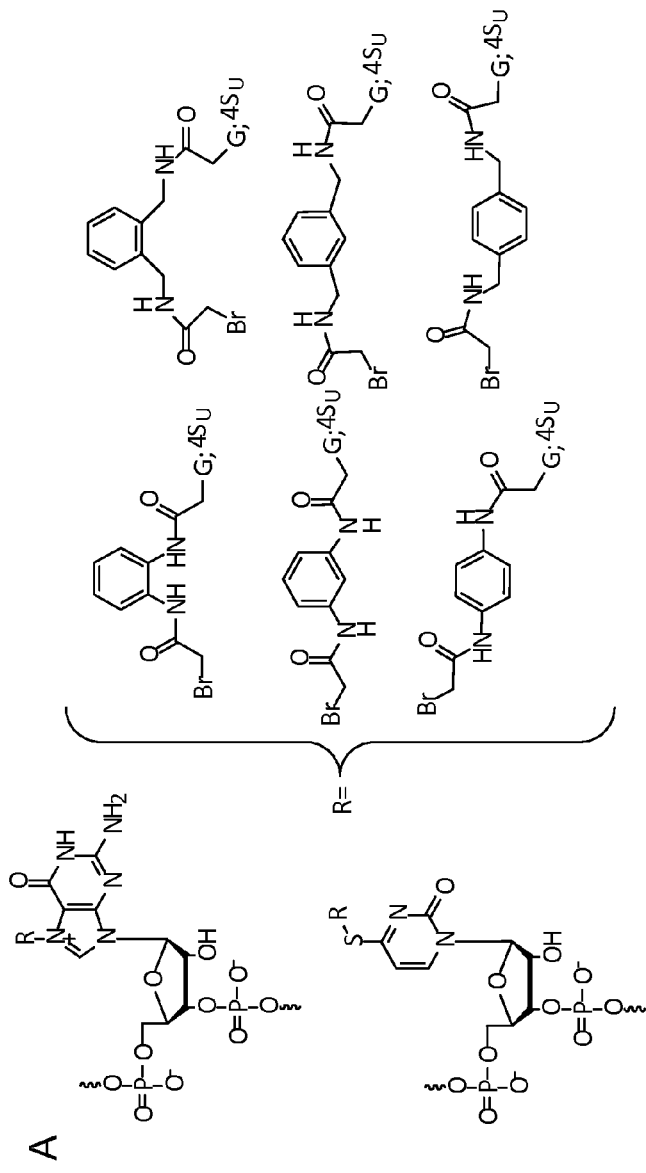
Figure 2:
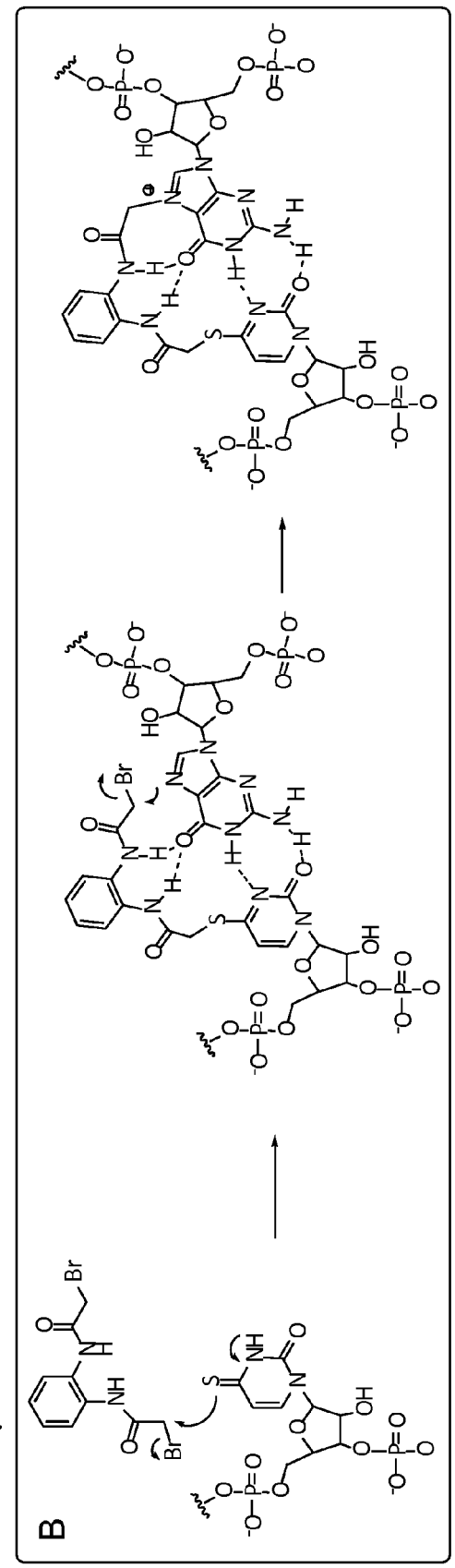

FIG. 2 depicts (A) the structures of various alkylated nucleosides and (B) an example of the crosslinking reaction between an alkylated nucleoside and a complementary reactive nucleoside. In (B), 4-thiouridine is first reacted with N,N'-bis-(bromoacetyl)-o-phenylenediamine (left). Upon base-pairing with a complementary guanosine, the remaining free alkylating group reacts with the N7 position of the guanosine, with the reaction promoted by hydrogen bonding between the guanosine C6 carbonyl group and the amide hydrogens of the reagent (center). The crosslinked product is shown on the right.

Figure 3:
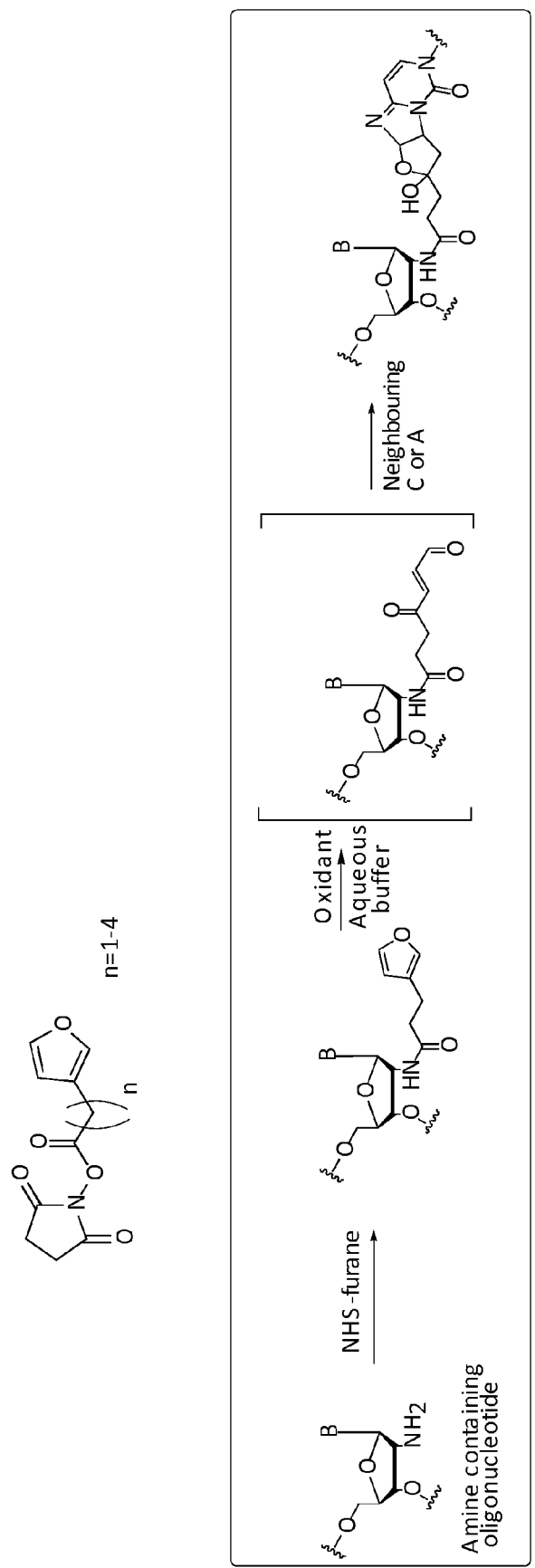

FIG. 3 shows the incorporation of a furan residue into an oligonucleotide and subsequent oxidation with N-bromosuccinimde (NBS), which leads to crosslinking to an adenosine or cytidine residue on the opposite strand.

Figure 4A:
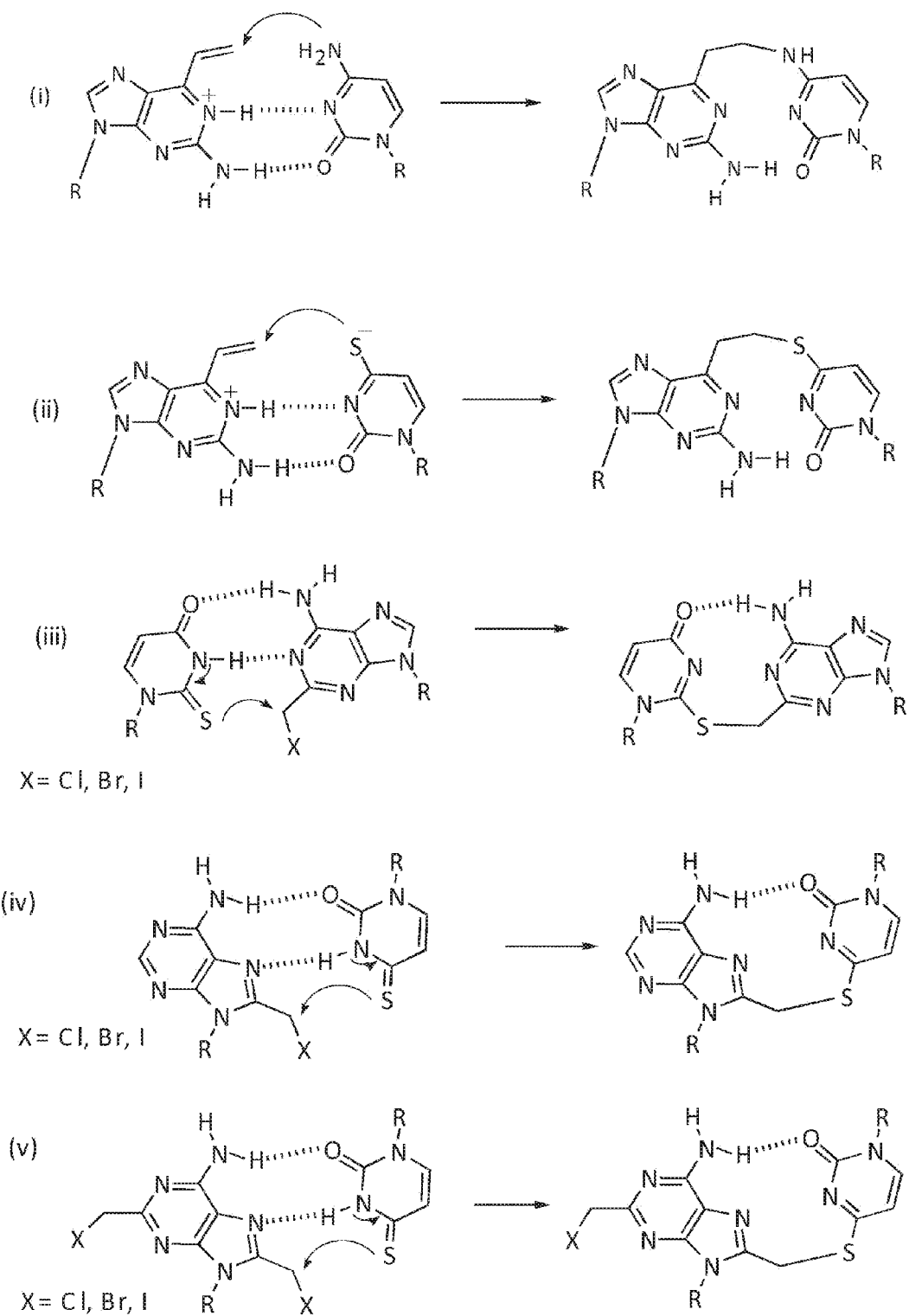
Figure 4B:
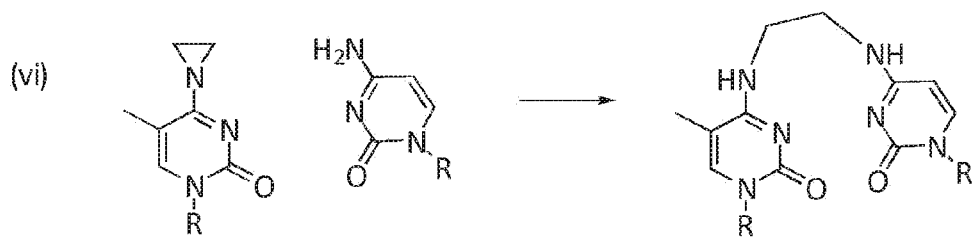
Figure 4B:
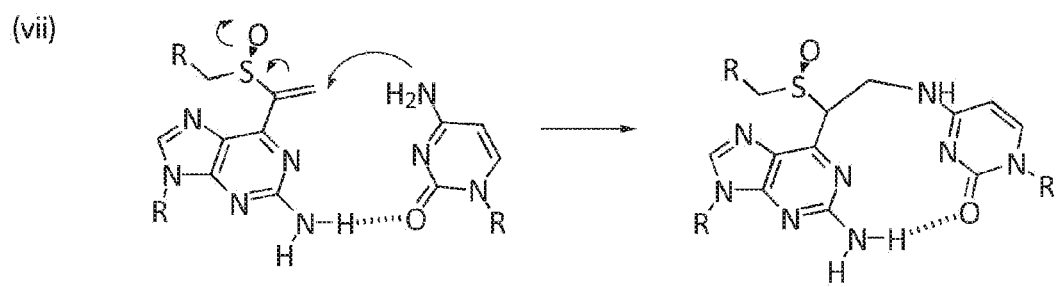
Figure 4B:
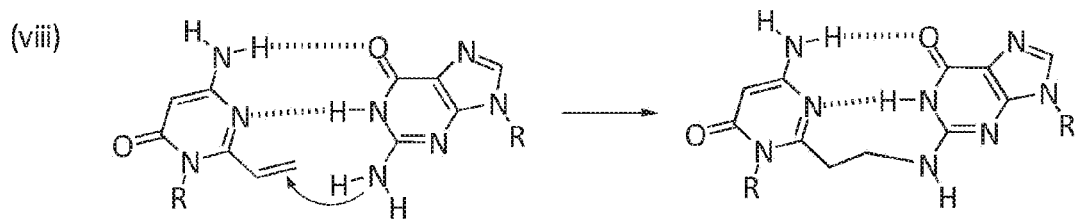
Figure 4B:
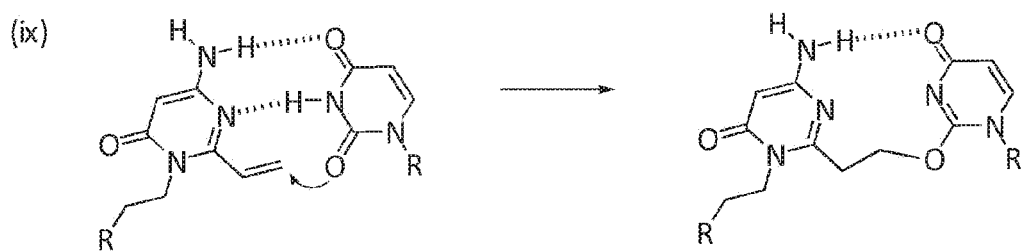

FIGS. 4A and 4B shows examples of pairs of an electrophilic nucleoside and its nucleophilic nucleoside partner: (i) 2-amino-6-vinylpurine and cytosine, (ii) 2-amino-6-vinylpurine and 4-thiouridine, (iii) 2-thiouridine and 2-alpha-halomethyl adenosine, (iv) 4-thiouridine and 8-alpha-halomethyl purine, (v) 4-thiouridine and 2,8-alpha-halomethyl purine, (vi) 5-methyl-$N^4,N^4$-ethanocytosine and cytosine, (vii) 2-amino-6-(1-ethylsulfinyl)vinyl purine nucleoside and cytosine, (viii) 4-amino-6-oxo-2-vinylpyrimidine nucleoside and guanine, and (ix) 4-amino-6-oxo-2-vinylpyrimidine-ethyl-C-nucleoside and uridine. R can be ribose, deoxyribose, or any suitable sugar (such as threose or glycerol) or a functional element (such as an amino acid) that is capable of forming a polymer.

Figure 5:
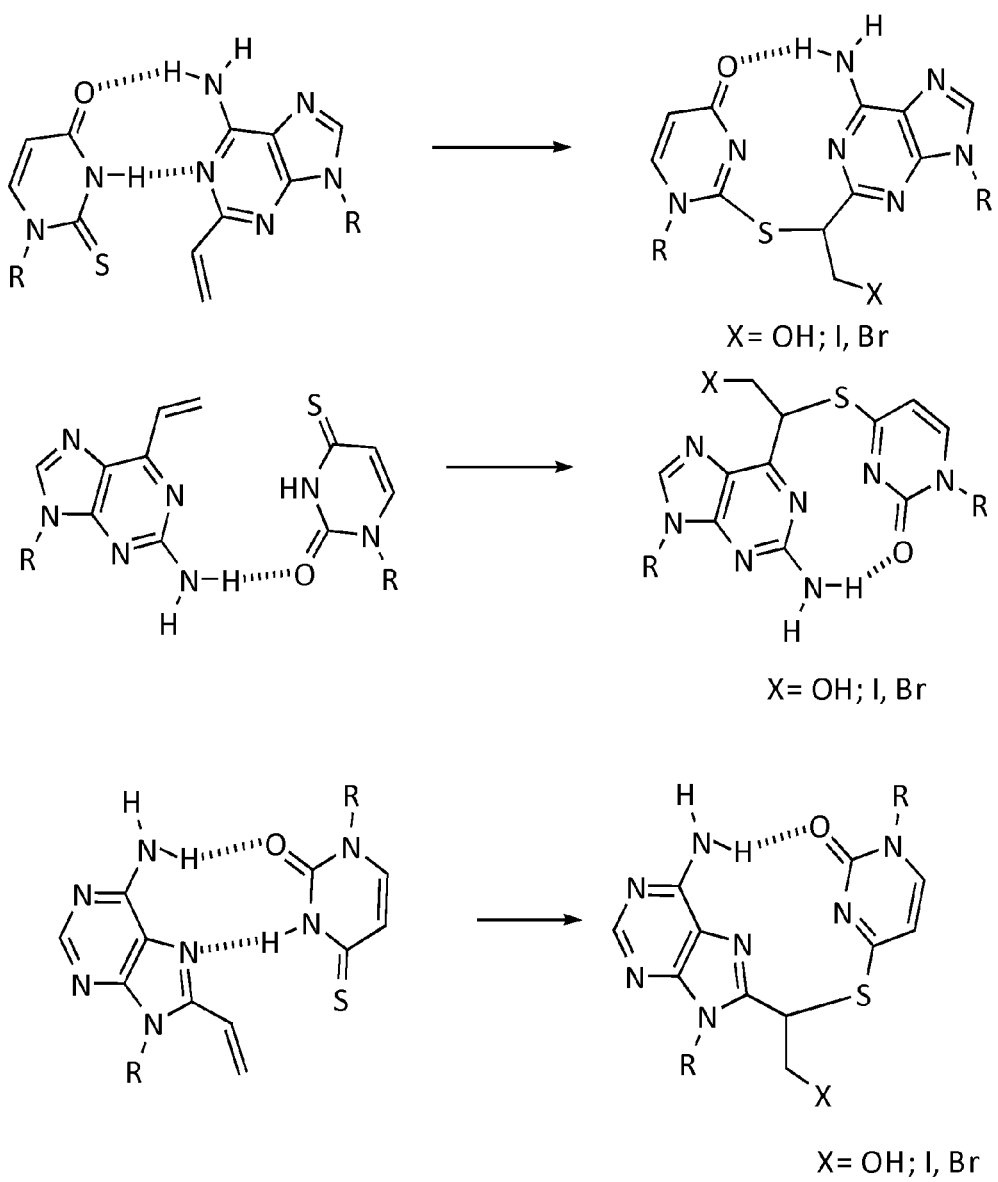

FIG. 5 depicts examples of complementary crosslinker pairs. Top: 2-thiouridine and an adenosine containing an olefin substitution at the 2-position of the purine ring. Middle: 4-thiouridine and 2-amino-6-vinylpurine. Bottom: 4-thiouridine and an adenosine containing a vinyl substituent at the 8-position of the purine ring.

Figure 6:
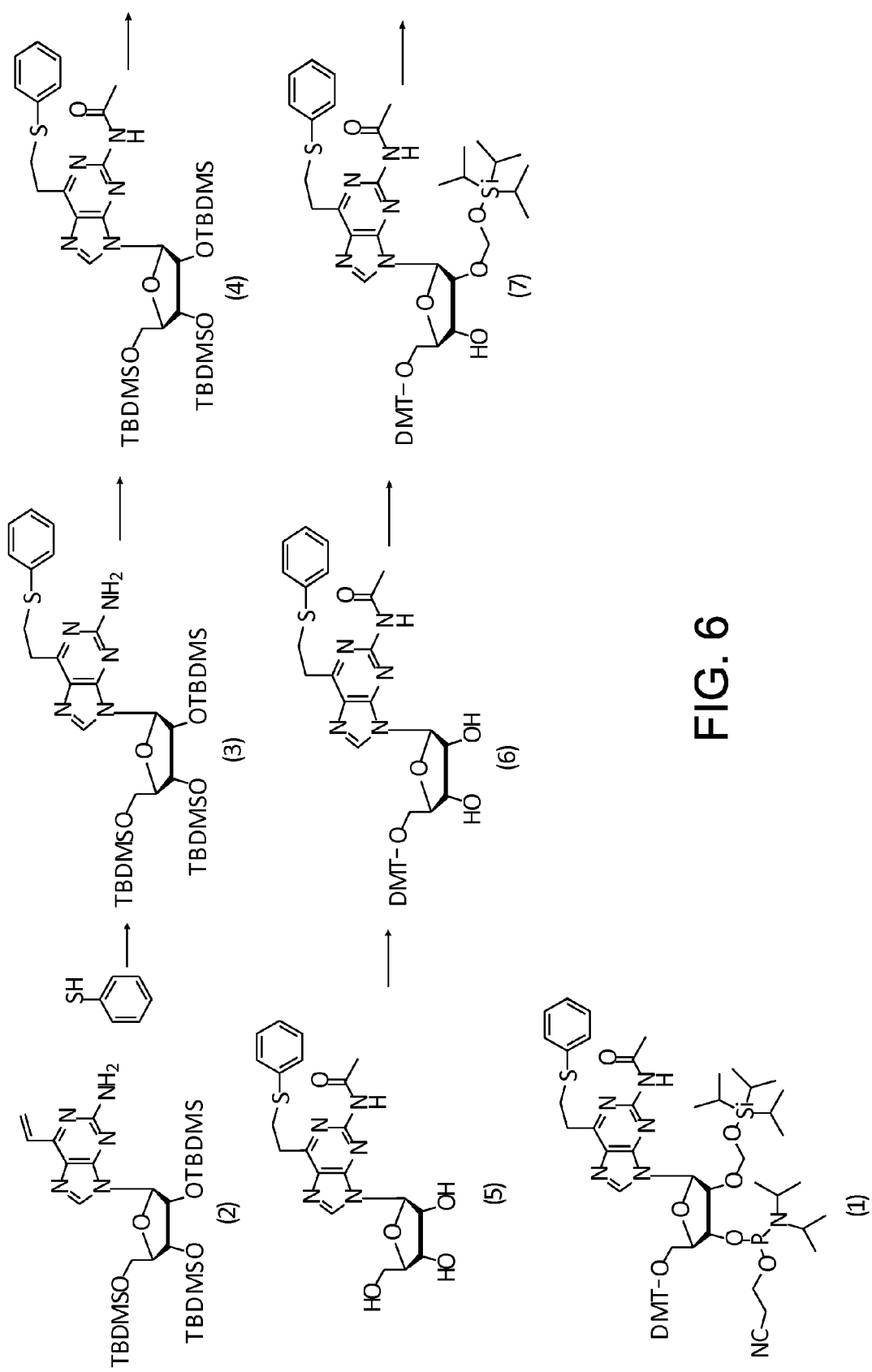

FIG. 6 illustrates the steps in an exemplary method for preparing a 2-amino-6-vinylpurine phosphoramidite.

Figure 7:
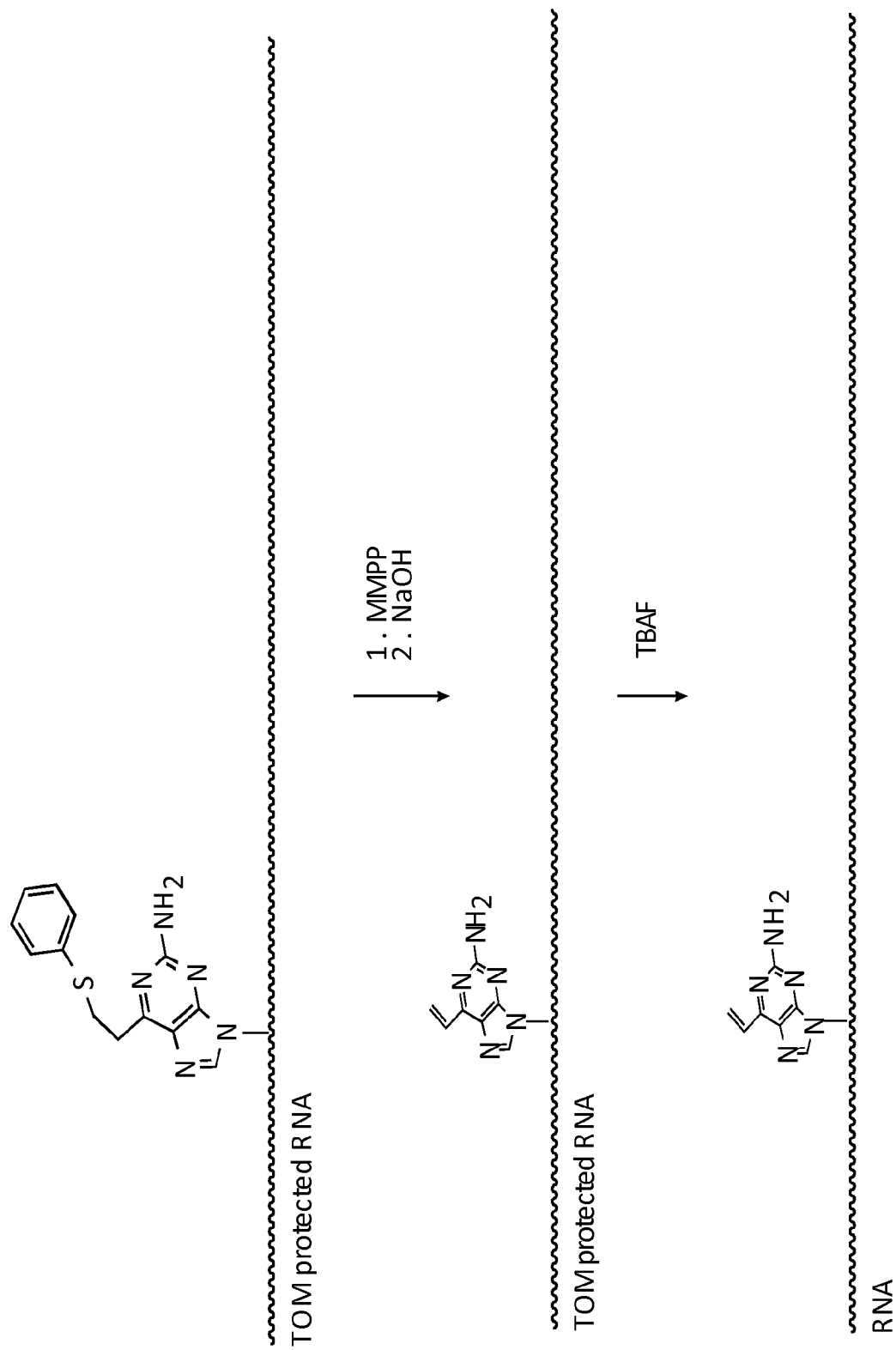

FIG. 7 shows the steps in an exemplary method for synthesizing oligonucleotides containing 2-amino-6 vinylpurine. The oligonucleotides can be ligated to an mRNA or portions of a linking tRNA molecule to produce reactive molecules suitable for practicing the present invention. (TOM: (triisopropylsilyl)oxy]methyl; MMPP: magnesium monoperphthalate; and TBAF: tetra-n-butylammonium fluoride.)

Figure 8A:
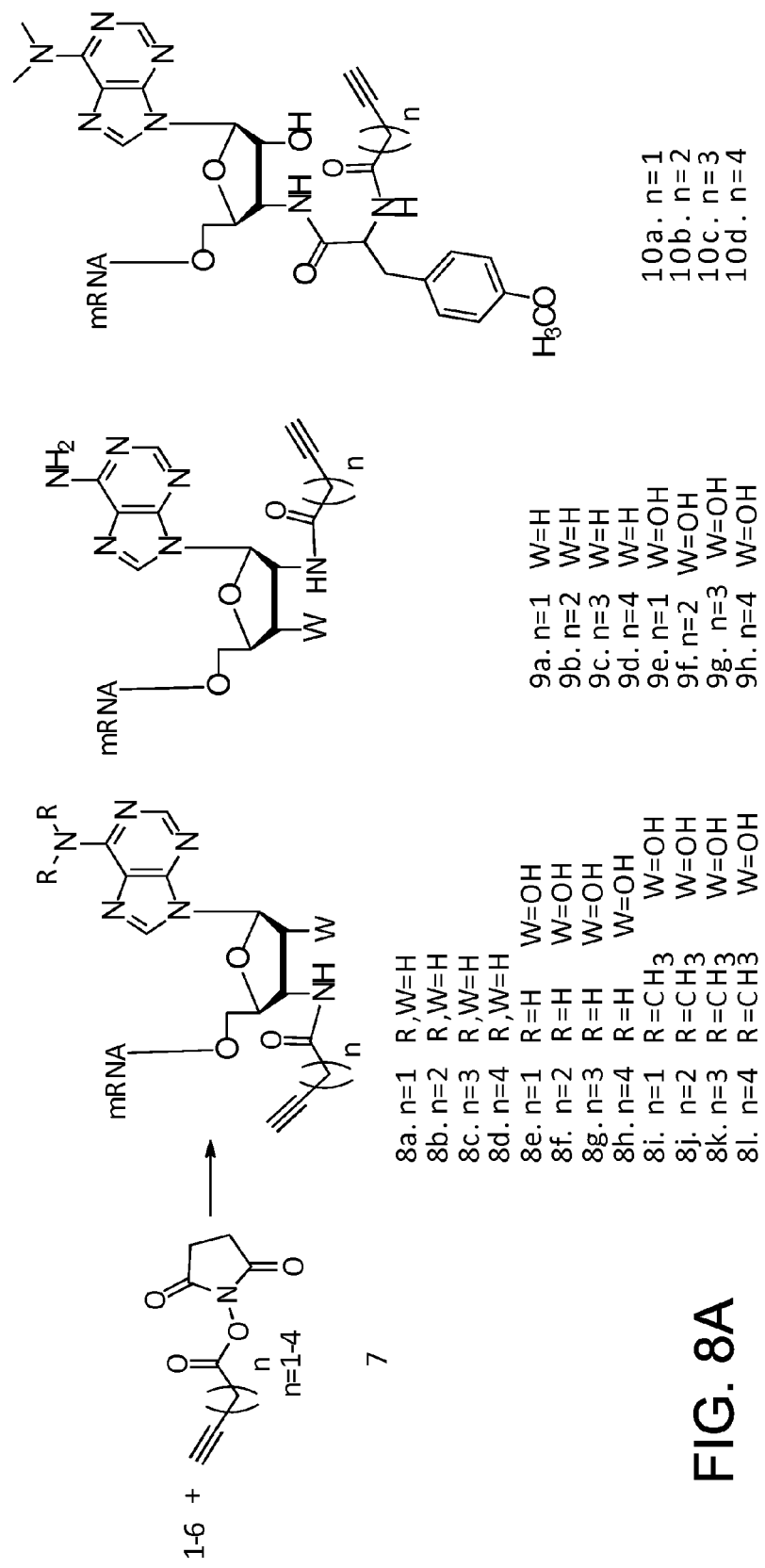
Figure 8B:
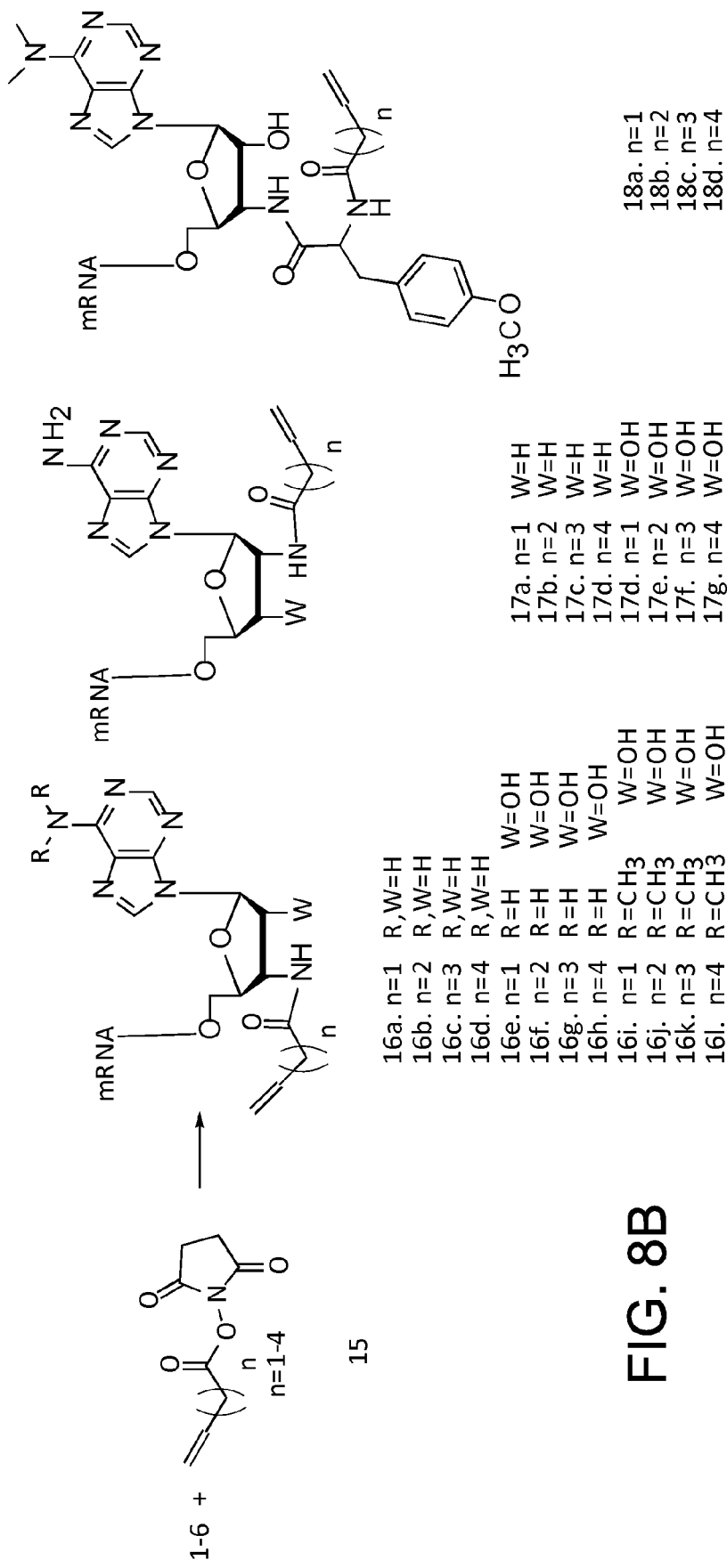
Figure 8C:
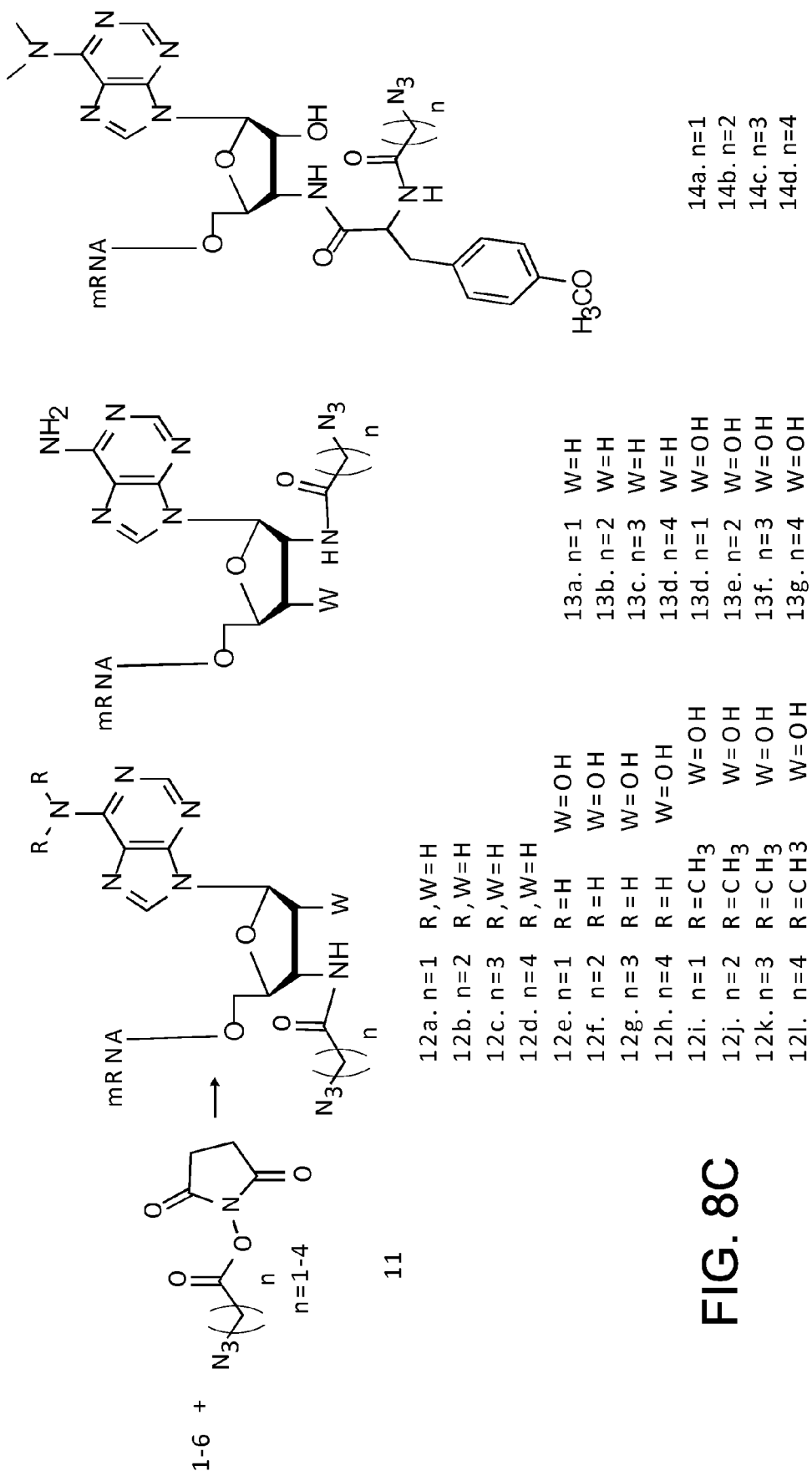
Figure 8D:
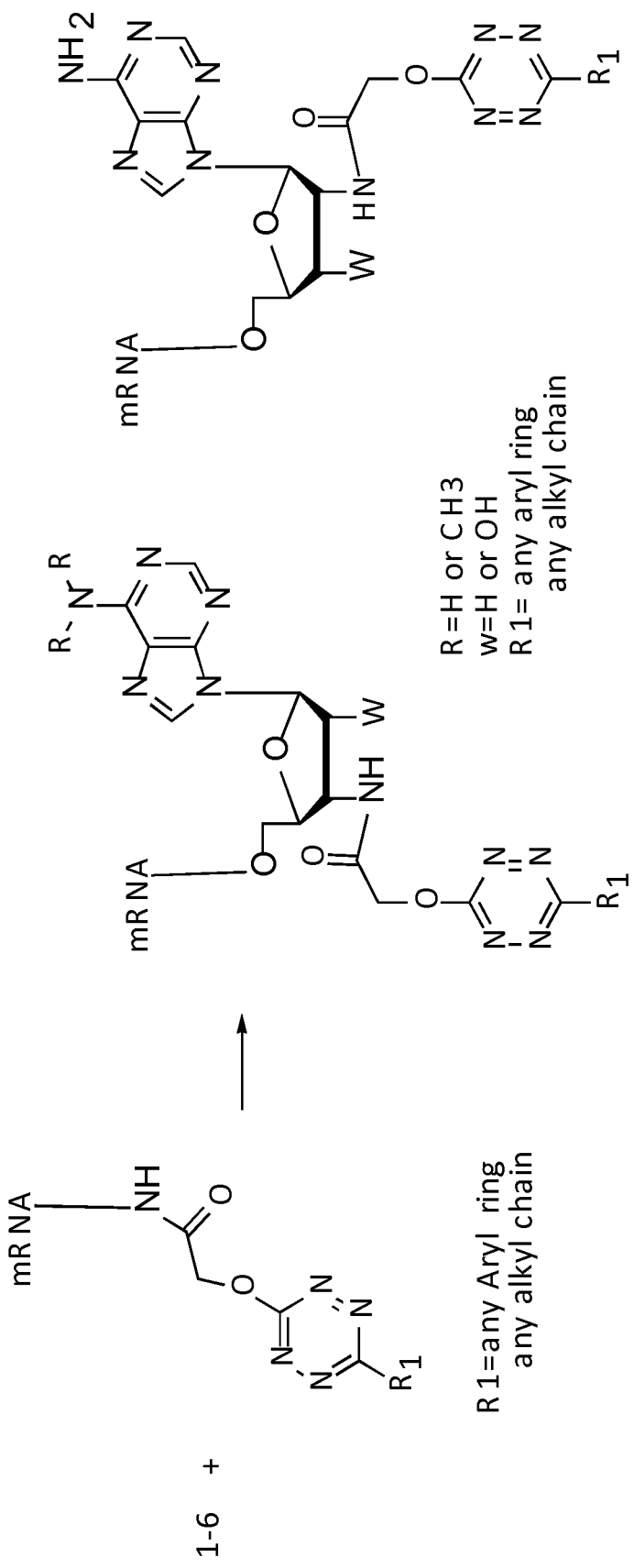
Figure 8E:
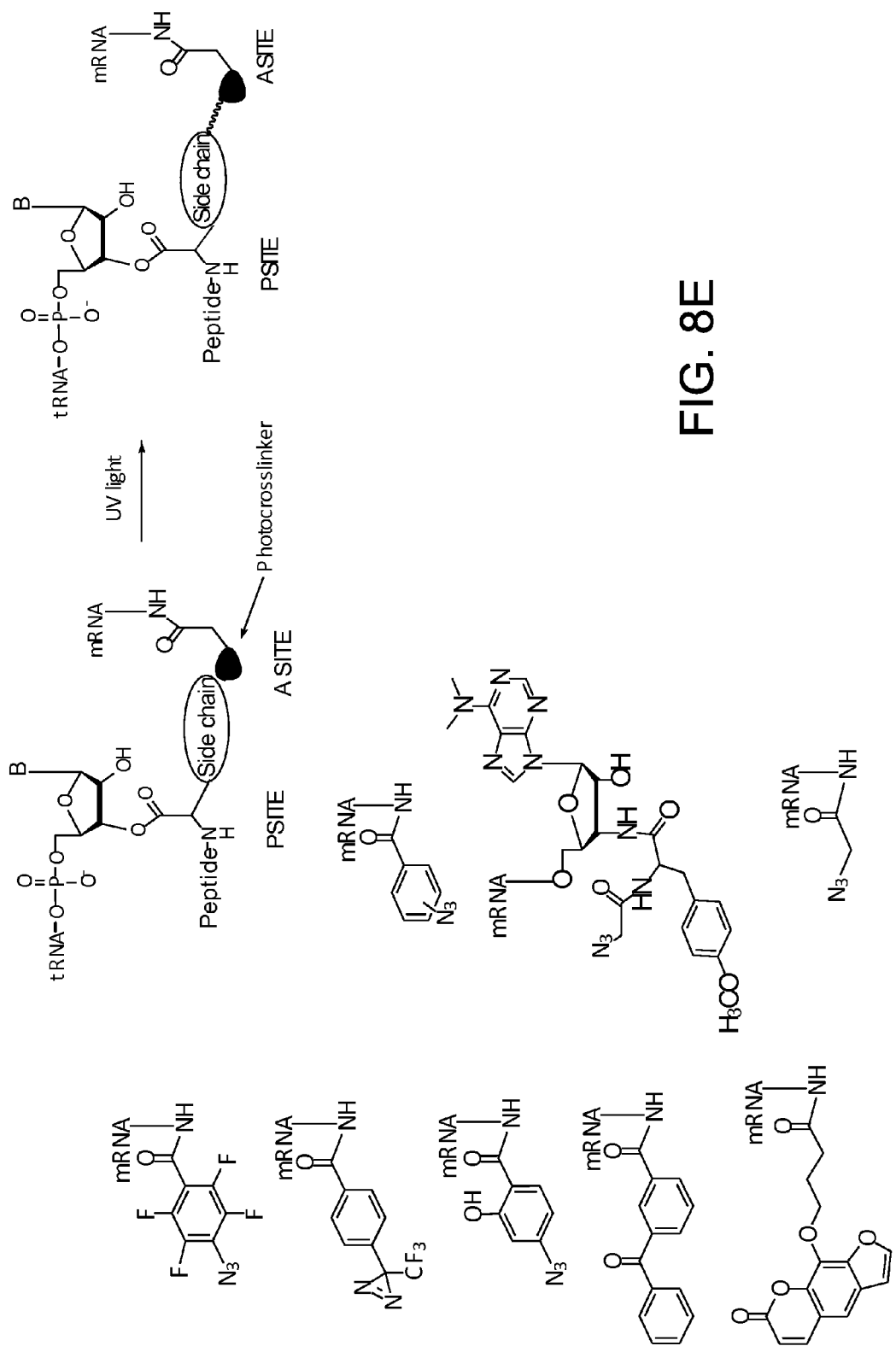
Figure 9A:
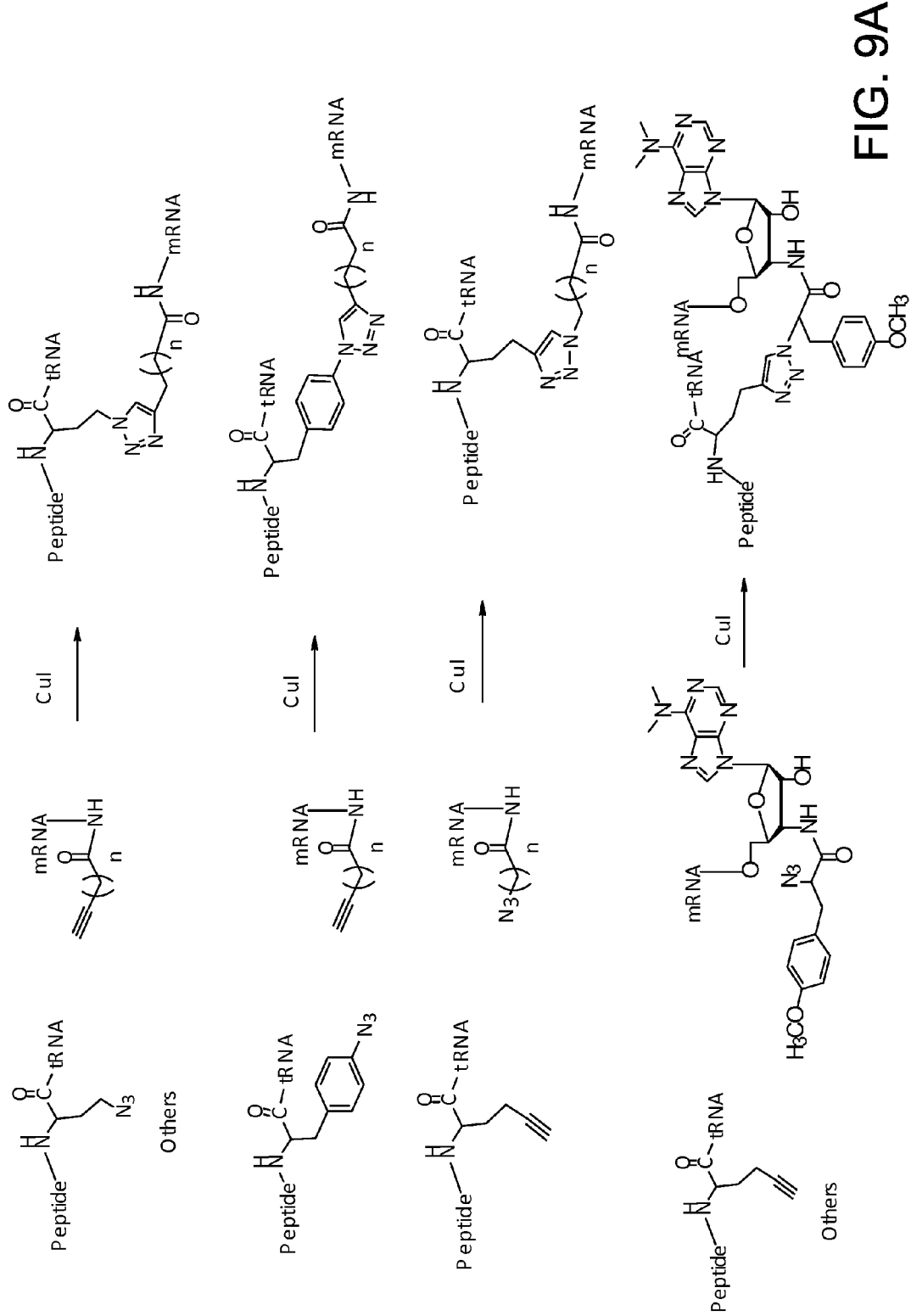
Figure 9B:
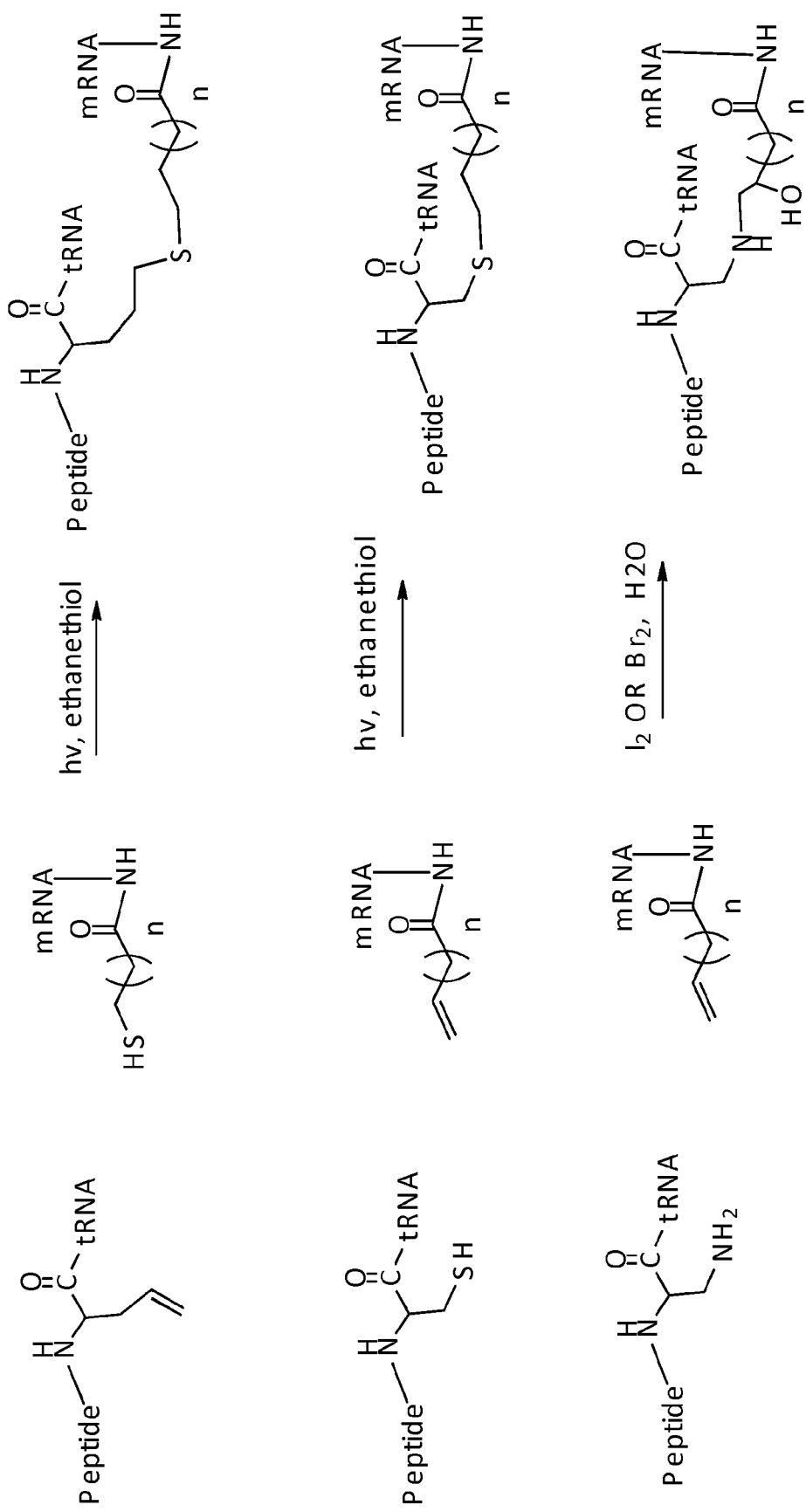
Figure 9C:
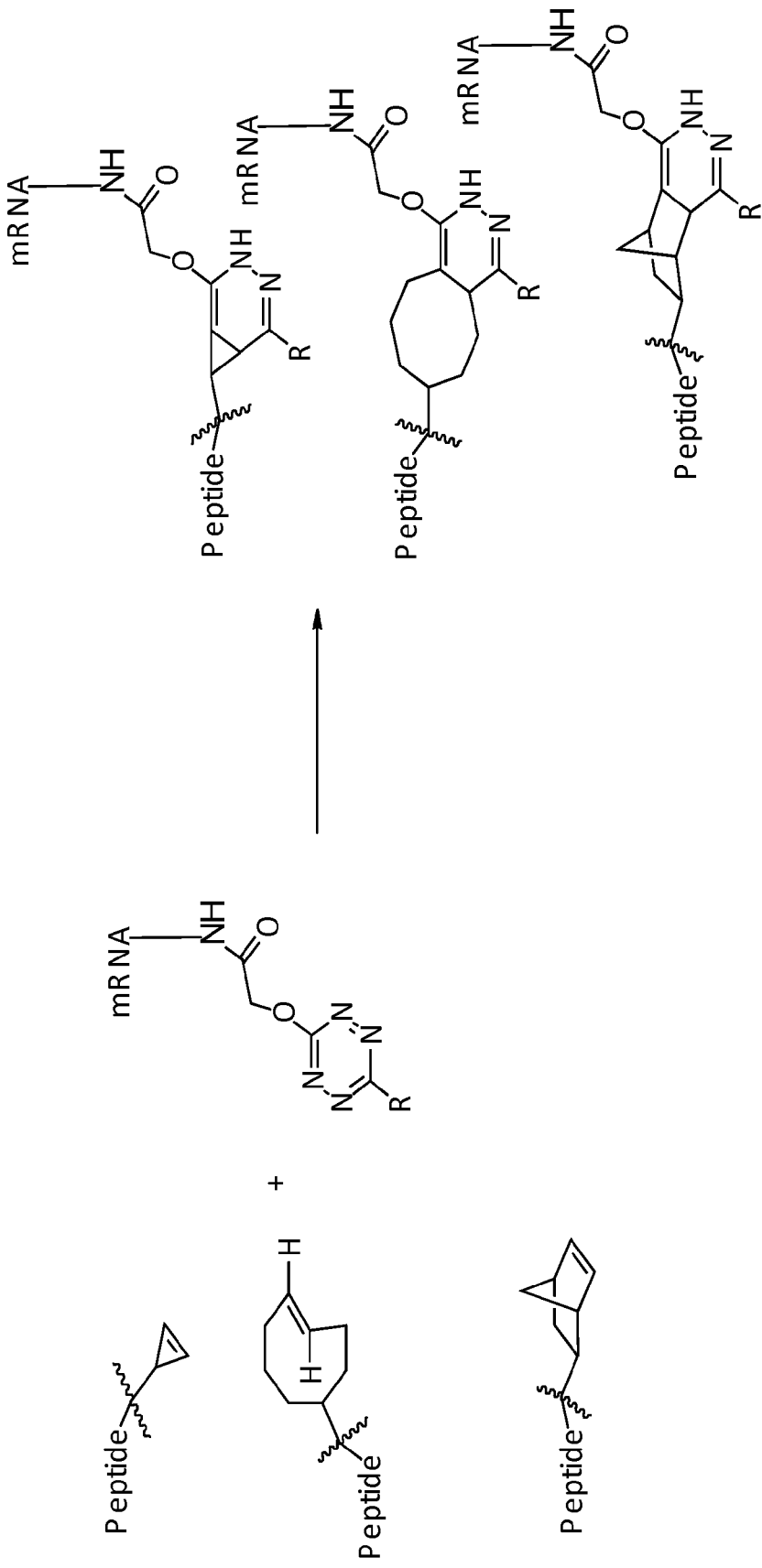

FIGS. 8A-E show exemplary linking moieties. FIG. 8A shows linking moieties containing an alkyne group; FIG. 8B shows linking moieties containing an alkene group; FIG. 8C shows linking moieties containing an azide group; FIG. 8D shows linking moieties containing a tetrazine group; and FIG. 8E shows linking moieties containing a photocrosslinker FIGS. 9A-C show exemplary bridging groups created between an mRNA and a polypeptide using different reactive pairs. FIG. 9A shows reactive pairs of an azide and an alkyne; FIG. 9B shows reactive pairs of an alkene and a thiol (first and middle) or an amine (bottom); FIG. 9C shows reactive pairs of a tetrazine and a cyclopropene (top), a trans-cyclooctene (middle), or a norbornene (bottom).

Figure 10C:
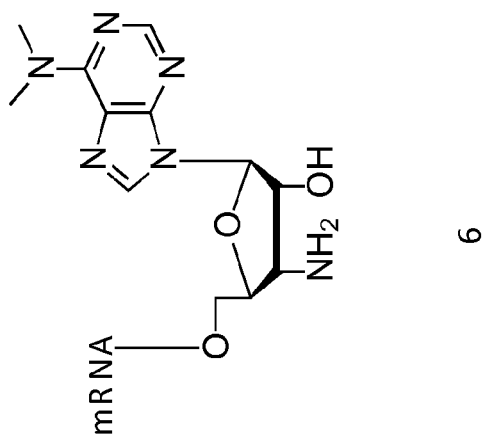
Figure 10B:
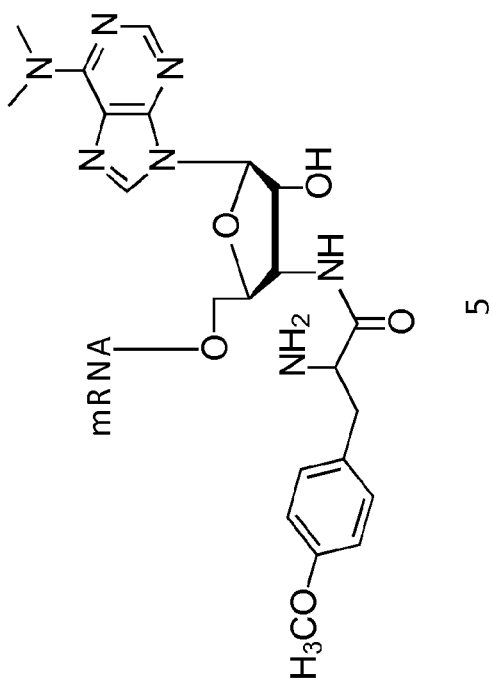
Figure 10A:
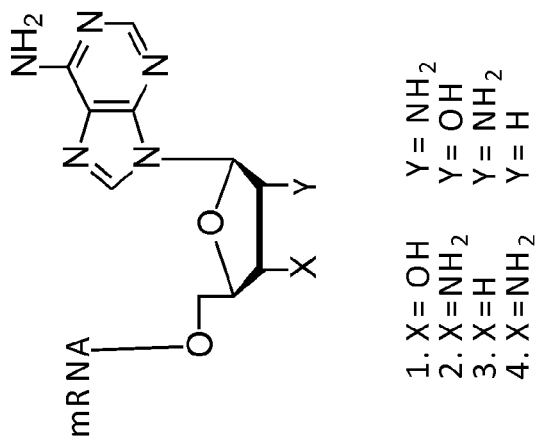

FIGS. 10A-C show exemplary 3'-terminal nucleotides containing an amino residue that can be modified with the different linking moieties shown in FIGS. 8A-E, or used to produce the functionalized RNAs described herein. FIG. 10A shows 2'-deoxy-2'-amino-adenosine (1), 3'-deoxy-3'-amino-adenosine (2), 2'-amino-2'-3'-dideoxy-adenosine (3), and 3'-amino-2'-3'-dideoxy-adenosine (4); FIG. 10B shows puromycin; and FIG. 10C shows 3'-amino-3'-deoxy-$N^6,N^6$-dimethyladenosine.

DETAILED DESCRIPTION

Described herein are tRNA molecules, mRNA molecules encoding a polypeptide, as well as novel methods for linking mRNA molecules to the polypeptides (e.g., a peptide or a protein) encoded by the mRNA molecules. The methods can be used to create vast libraries of polypeptides from which those with desired target binding or other target-specific activities can be selected along with their encoding mRNA. The invention can also be applied to in vitro evolution of polypeptides in order to optimize their binding affinities or other properties.

Methods of Linking an mRNA Molecule to a Polypeptide

Two general approaches are described to link a polypeptide to its encoding mRNA. In one method, the mRNA is indirectly linked to the polypeptide through a linking tRNA. In a second method, the mRNA is linked to the polypeptide through a chemical or photochemical reaction between the terminus of the mRNA molecule and a portion of the polypeptide chain.

Linking a Polypeptide to an Encoding mRNA Through a tRNA

In one approach for linking an mRNA molecule to a polypeptide, the mRNA molecule and the polypeptide become linked through a tRNA, forming an mRNA-tRNA-polypeptide complex. A tRNA that links an mRNA to a polypeptide is referred to herein as a "linking tRNA."

As used herein, by "a" is meant at least one. As used herein, a nucleoside includes a nucleobase (or "base") bound to a ribose or deoxyribose sugar. A nucleoside can be a naturally-occurring nucleoside (i.e., cytosine, adenosine, guanosine, thymidine, or uridine) or a modified nucleoside that differs from a naturally-occurring nucleoside in the structure of its nucleobase and/or sugar. The nucleobase can be bound to other sugars, such as threose, or other polymer-forming molecules, such as glycerol or an amino acid.

Generally, the methods involve using an mRNA or a linking tRNA molecule that contains at least one (e.g., two, three, or four) crosslinker or reactive nucleoside that can crosslink with a nucleoside (e.g., a natural or modified nucleoside that is reactive with the crosslinker or reactive nucleoside) in a linking tRNA or an mRNA, respectively. The term "crosslinker" refers to any moiety that can be used to covalently link two molecules together via a chemical reaction between (a) the moiety on one molecule and (b) a second molecule. In non-limiting examples, a crosslinker can be a modified nucleoside or a moiety on a natural or modified nucleoside. Crosslinking between two molecules can occur spontaneously, or by adding an agent or performing a treatment that induces crosslinking Additional examples of crosslinkers are described herein. A reactive nucleoside can include any of the natural or modified nucleosides described herein.

Figure 1:
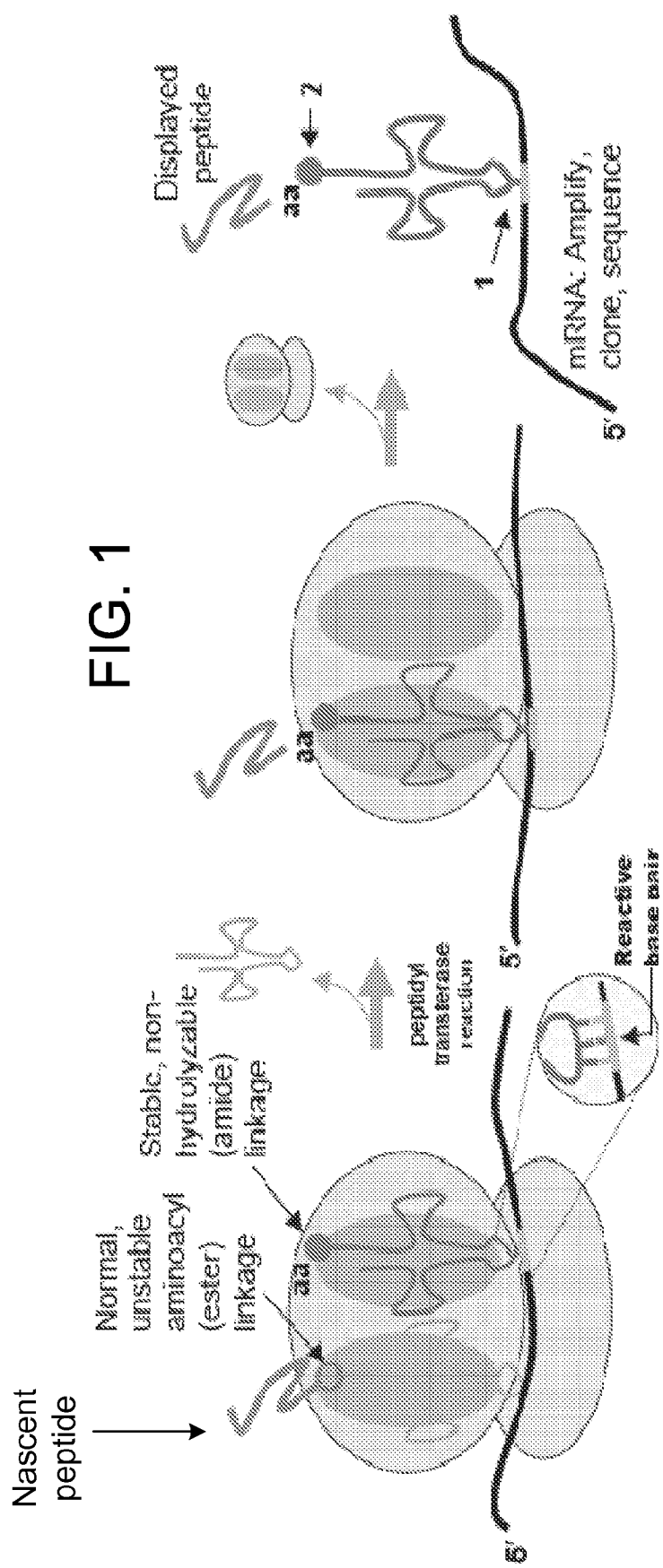
FIG. 1 shows an exemplary strategy for linking an mRNA molecule to a polypeptide encoded by the mRNA. In this diagram, the reactive base pair is on the mRNA, but it may be present on the linking tRNA also, with the same final result. Furthermore, in this diagram the covalent bond between the linking tRNA and the amino acid is an amide. It is appreciated by those skilled in the art that other types of covalent bonds, including an ester bond, can be used so long as reasonable care is taken to preserve the bridging group (e.g., avoiding prolonged exposure to elevated temperature, exposure to acidic or basic conditions incompatible with ester bonds).

An mRNA (e.g, one containing at least one crosslinker or reactive nucleoside) described herein is translated to produce a polypeptide using an in vitro translation system, as described in more detail below. A linking aminoacyl-tRNA includes a linking tRNA and an aminoacyl residue attached to the linking tRNA by a stable, non-hydrolyzable covalent bond. An example of such a bond is an amide bond. Those skilled in the art will appreciate that a less stable ester bond may also be used as long as measures are taken to protect it from hydrolysis (e.g., avoiding prolonged exposure to elevated temperatures or acidic or basic conditions that are incompatible with an ester bridging group). If the mRNA does not contain a crosslinker or reactive nucleoside), then the crosslinker or reactive nucleoside is present on the linking tRNA. After the linking aminoacyl-tRNA accepts the nascent polypeptide by the action of the ribosome's peptidyl transferase, the nascent polypeptide will remain attached to the linking tRNA. Upon crosslinking of the crosslinker or reactive nucleoside in the mRNA to a nucleoside in the linking tRNA, or upon crosslinking of the crosslinker or reactive nucleoside in the linking tRNA to a nucleoside in the mRNA, the linking tRNA and the mRNA become covalently linked, and a covalent linkage of the polypeptide to the mRNA through the linking tRNA is created. FIG. 1 illustrates an exemplary strategy for linking an mRNA molecule to a polypeptide encoded by the mRNA. In FIG. 1, the crosslinker (e.g., the reactive base) is shown as positioned in the mRNA, but it may be present on the linking tRNA instead.

Generally, when a crosslinker or reactive nucleoside is in the mRNA, it is positioned at (or within one to three bases from) the end of the polypeptide coding region of the mRNA molecule. The crosslinker or reactive nucleoside can be positioned in an in-frame codon encoding an amino acid or in an in-frame stop codon, or can be in a nucleotide that is within one to three bases 3' to a stop codon at the end of the coding region. In most cases, crosslinking between the crosslinker or reactive nucleoside in the mRNA and a nucleoside in the linking tRNA requires specific pairing between the codon containing the crosslinker or reactive nucleoside and its corresponding anticodon in the linking tRNA during translation of the mRNA. In other cases, as described herein, the crosslinker or reactive nucleoside does not have to be in a codon recognized by the anticodon of the linking tRNA. For example, the crosslinker or reactive nucleoside can be positioned near (e.g., within one to three bases from) a codon in the mRNA that corresponds to the anticodon of the linking tRNA. In some embodiments, the mRNA molecule or the linking tRNA can include more than one (e.g. two, three, or four) of the same crosslinker, or multiple different crosslinkers. Optimized configurations of the number and/or positions of crosslinkers can be determined by creating mRNAs or linking tRNAs with different configurations and assaying the yield of crosslinked mRNA-tRNA-polypeptide complexes, e.g., by electrophoresis.

A linking tRNA can contain one or more (e.g., two, three, or four) natural or modified nucleosides (e.g., activated nucleosides) or crosslinkers that can react with a nucleoside (e.g., a reactive nucleoside) in an mRNA molecule, such that the linking tRNA can be covalently linked to the mRNA molecule. A reactive nucleoside can be a nucleoside that is reactive with an activated or modified nucleoside, or crosslinker Generally, but not always, the nucleoside or crosslinker that can react with a crosslinker or a nucleoside on the mRNA is positioned in the anticodon of the linking tRNA. The linking tRNA can be a native, modified, or synthetic tRNA. The anticodon of the linking tRNA can be one that recognizes a sense or stop codon. In some embodiments, the linking tRNA recognizes a sense codon that immediately precedes one or more stop codons. In some embodiments, the linking tRNA recognizes a stop codon. The term "suppressor tRNA" refers to a tRNA that recognizes a stop codon. In some embodiments, the linking tRNA contains at least one (e.g., two, three, or four) activated nucleoside (e.g., a crosslinker or modified nucleoside) and the mRNA contains at least one (e.g., two, three, or four) natural or modified reactive nucleosides that can crosslink to at least one (e.g., one, two, three, or four) activated nucleoside in the linking tRNA. In other embodiments, the anticodon of the linking tRNA is a four-base sequence that recognizes a four-base codon in an mRNA. When the crosslinker is located in an anticodon of a linking tRNA that encodes an amino acid, the mRNA can be designed such that the corresponding codon only occurs once in the mRNA (i.e., at the site at which crosslinking is desired).

The methods described herein allow the production of mRNA-tRNA-polypeptide complexes. Non-limiting examples of mRNA-tRNA-polypeptide complexes that are provided herein contain an mRNA covalently linked to a tRNA that is covalently linked to an amino acid in a polypeptide, where the mRNA is linked to the tRNA via a bridging group selected from the group of: N-7 alkylpurine, oxadiazabicyclo[3.3.0]octaimine, 4-aminoalkylpyrimidine, 4-thioalkylpyrimidine, 2-thioalkylpyrimidine, 2-aminoalkylpyrimidine, 4-alkyloxypyrimidine, an ether, a thioether, and a secondary amine. Also provided herein are libraries containing a plurality of these mRNA-tRNA-polypeptide complexes, where the mRNA of each mRNA-tRNA-polypeptide complex encodes a different polypeptide. In some embodiments, libraries containing a plurality of these mRNA-tRNA-polypeptide complexes contain different mRNA-tRNA-polypeptide complexes. These libraries can be used to screen for a polypeptide that interacts with a target. Non-limiting examples of screening methods are described herein. An example of such screening methods include: (a) providing any of the libraries containing a plurality of mRNA-tRNA-polypeptide complexes described herein; (b) contacting the library with the target; and (c) selecting an mRNA-tRNA-polypeptide complex containing a polypeptide that interacts with the target. Additional methods of using mRNA-tRNA-polypeptide complexes are described herein and may be used in any combination without limitation.

Crosslinking between an Alkylated Nucleoside and its Reactive Nucleoside

One method for covalently linking an mRNA molecule to a linking tRNA involves crosslinking at least one (e.g., two, three, or four) alkylated nucleoside in the mRNA to at least one (e.g., two, three, or four) reactive nucleoside (e.g., one that reacts with the alkylated nucleoside) positioned in the anticodon of the linking tRNA. An example of the crosslinking reaction between an alkylated nucleoside and its reactive nucleoside is illustrated in FIG. 2. Crosslinking of an alkylated nucleoside to its reactive nucleoside occurs spontaneously, e.g., without requiring the addition of an agent or treatment to induce crosslinking. Preferably, the alkylated nucleoside and its reactive nucleoside are complementary nucleosides so as to take advantage of the geometry of their normal hydrogen bond pairing to increase the effective molarity and drive the reaction to completion. Inter-strand crosslinking of a 4-thiouridine residue with a complementary guanosine residue in DNA has been described (see, Coleman, R. S, and Kesicki, E. A., *J. Org. Chem.* 60:6252-6253, 1995; and Coleman, R. S, and Pies, R. M., *Nucl. Acids. Res.* 25:4771-4777, 1997). Alternatively, the alkylated nucleoside can be in the anticodon of the linking tRNA and the reactive nucleoside can be in the mRNA (e.g., in the corresponding codon).

Those of ordinary skill in the art would understand that there are many possible combinations of an alkylated nucleoside and its reactive nucleoside. For example, an alkylated 4-thiouridine can be crosslinked to its reactive nucleoside, such as guanosine. Alternatively, an alkylated guanosine can be crosslinked to its reactive nucloside, such as 4-thiouridine. The alkylated guanosine can be an N-7 alkylated guanosine. The N-7 alkylated guanosine can contain, for example, one of the following at the N-7 position of the guanosine nucleoside: N-(2-acetamidophenyl)-2-bromoacetamide, N-(3-acetamidophenyl)-2-bromoacetamide, N-(4-acetamidophenyl)-2-bromoacetamide, N-((2-acetamidomethyl)benzyl)-2-bromoacetamide, N-((3-acetamidomethyl)benzyl)-2-bromoacetamide, N-((4-acetamidomethyl)benzyl)-2-bromoacetamide, (Z/E)-N-(4-acetamidobut-2-enyl)-2-bromoacetamide, or (Z/E)-N-(2-acetamidovinyl)-2-bromoacetamide.

In some embodiments, an S-4-alkylated thiouridine and its reactive nucleoside, e.g., guanosine, can be used to link the mRNA to the linking tRNA. The S-4 alkylated uridine can include one of the following at the S-4 position of the nucleoside: N-(2-acetamidophenyl)-2-bromoacetamide, N-(3-acetamidophenyl)-2-bromoacetamide, N-(4-acetamidophenyl)-2-bromoacetamide, N-((2-acetamidomethyl)benzyl)-2-bromoacetamide, N-((3-acetamidomethyl)benzyl)-2- bromoacetamide, N-((4-acetamidomethyl)benzyl)-2-bromoacetamide, (Z/E)-N-(4-acetamidobut-2-enyl)-2-bromoacetamide, or (Z/E)-N-(2-acetamidovinyl)-2-bromoacetamide.

An mRNA containing an alkylated nucleoside can be generated using methods known in the art and described herein (e.g., in Example 1 below). Typically, the mRNA molecule contains one to three alkylated residues (e.g., at the 3' end of the mRNA or at the 3' end of the polypeptide coding region) that can crosslink with one to three reactive nucleosides in the anticodon of the linking tRNA.

Whichever combination of alkylated nucleoside and reactive nucleoside is chosen, it is understood that the alkylated nucleoside(s) can be present on the linking tRNA and a suitable reactive nucleoside(s) can be present on the mRNA.

Crosslinking Using a 4-oxo-2-pentenal Moiety

Another method for linking a coding molecule to a linking tRNA involves crosslinking at least one (e.g., two, three, or four) 4-oxo-2-pentenal moiety in the mRNA to at least one (e.g., two, three, or four) nucleoside, typically an adenosine or a cytidine, in the linking tRNA. This method does not require specific pairing between a nucleoside containing a 4-oxo-2-pentenal moiety and a complementary nucleoside in the anticodon of the linking tRNA. For example, the 4-oxo-2-pentenal moiety can be attached to a nucleoside positioned near (e.g., within one or two bases of) a codon that is recognized by the anticodon (which contains an adenosine or a cytidine) of the linking tRNA. In another possible configuration, the nucleoside containing a 4-oxo-pentenal moiety is in a codon recognized by the anticodon of the linking tRNA, and the adenosine or cytidine residue that can react with the 4-oxo-pentenal moiety is positioned adjacent to the anticodon (e.g., in a nucleoside that is one or two residues away from the anticodon).

An mRNA containing a 4-oxo-2-pentenal moiety can be created by first reacting an mRNA molecule containing, for example, a 2'-amino nucleoside with an N-hydroxysuccinimide ester of an alkyl furan to incorporate a furan moiety into the mRNA, and then treating the mRNA with an oxidizing agent to generate a 4-oxo-2-pentenal moiety on the mRNA. Alkyl furans with different linker sizes can be used. For example, the alkyl furan can be 2-(furan-3-yl) acetic acid, 3-(furan-3-yl) propanoic acid, or 4-(furan-3-yl) butanoic acid. Oxidizing agents that can be used include, but are not limited to, N-bromosuccinimide (NBS), meta-chloro peroxybenzoic acid, methylene blue, molecular oxygen, bromine, and ultraviolet light.

Once a 4-oxo-2-pentenal moiety is created on an mRNA or tRNA, the moiety can spontaneously react (e.g., without adding an agent or treatment to induce the reaction) with an adenosine or a cytidine in the linking tRNA or mRNA during or after translation of the mRNA. Thus, an mRNA or tRNA molecule with at least one 4-oxo-2-pentenal moiety can be created before the mRNA is translated using a translation system. Alternatively, a translation system including an oxidizing agent can be used to translate an mRNA molecule that comprises a furan moiety to create a 4-oxo-pentenal moiety on the mRNA during translation. In yet another option, the oxidizing agent can be added during or after translation of an mRNA containing a furan moiety.

The 4-oxo-2-pentenal moiety can also be present on the linking tRNA such that it reacts with an adenosine or a cytidine in the mRNA. This method does not require specific pairing between a nucleoside containing a 4-oxo-2-pentenal moiety and a complementary nucleoside in the corresponding codon of the mRNA. The 4-oxo-2-pentenal moiety can be attached to a nucleoside positioned near (e.g., within one or two bases of) the anticodon of the linking tRNA that corresponds to a codon of the mRNA. In another possible configuration, the nucleoside containing a 4-oxo-pentenal moiety is in the anticodon of the linking tRNA, and the adenosine or cytidine residue that can react with the 4-oxo-pentenal moiety is positioned adjacent to corresponding codon of the mRNA (e.g., in a nucleoside that is one or two residues away from the codon).

A linking tRNA containing at least one 4-oxo-2-pentenal moiety can be created by first reacting a linking tRNA molecule or a portion of a linking tRNA molecule comprising, for example, a 2'-amino nucleoside with an N-hydroxysuccinimide ester of an alkyl furan to incorporate a furan moiety into the linking tRNA or portion thereof, and then treating the linking tRNA or portion thereof with an oxidizing agent to generate a 4-oxo-2-pentenal moiety on the linking tRNA or portion thereof. Alkyl furans with different linker sizes can be used. For example, the alkyl furan can be 2-(furan-3-yl) acetic acid, 3-(furan-3-yl) propanoic acid, or 4-(furan-3-yl) butanoic acid. Oxidizing agents include, but are not limited to, N-bromosuccinimide (NBS), meta-chloro peroxybenzoic acid, methylene blue, molecular oxygen, bromine, and ultraviolet light.

As described above for 4-oxo-2-pentenal-modified mRNA, a linking tRNA molecule with at least one 4-oxo-2-pentenal moiety can be created before the linking tRNA is used in a translation system. Alternatively, a translation system including an oxidizing agent can be used to convert a linking tRNA molecule containing a furan moiety to a 4-oxo-pentenal moiety during translation, or the oxidizing agent can be added after translation.

An illustration of exemplary reactions involved in using a 4-oxo-2-pentenal moiety to link an mRNA molecule to a linking tRNA is shown in FIG. 3.

Crosslinking between an Electrophilic Nucleoside and its Nucleophilic Nucleoside Partner Via Hybridization Triggered Alkylation Yet another strategy for linking an mRNA molecule to a linking tRNA involves crosslinking between an electrophilic nucleoside and its nucleophilic nucleoside partner via hybridization-triggered alkylation. As used herein, "hybridization-triggered alkylation" refers to the covalent linking of two nucleosides, one containing an electrophilic nucleobase and the other containing a nucleophilic nucleobase, that occurs as a result of the two nucleosides interacting via non-covalent hydrogen bonding. See, Webb, T. R. and Matteucci, M. D., *Nucl. Acids. Res.* 14:7661-7674, 1986; Webb, T. R. and Matteucci, M. D., *J. Am. Chem. Soc.* 108:2764-2765, 1986. Thus, an electrophilic nucleoside and its nucleophilic nucleoside partner will frequently be complementary nucleobases. Those of ordinary skill in the art will appreciate that the electrophilic nucleoside can be in the mRNA and its nucleophilic nucleoside partner can be in the anticodon of the linking tRNA, or vice versa. FIG. 4 shows examples of electrophilic nucleosides and their nucleophilic nucleoside partners.

Pairs of electrophilic and nucleophilic nucleoside partners include, but are not limited to, 2-amino-6-vinylpurine and cytosine, 2-amino-6-vinylpurine and 4-thiouridine, 2-alpha-halomethyl adenosine and 2-thiouridine, 8-alpha-halomethyl purine and 4-thiouridine, 2,8-alpha-halomethyl purine and 4-thiouridine, 5-methyl-$N^4,N^4$-ethanocytosine and cytosine; 2-amino-6-(1-ethylsulfinyl)vinyl purine nucleoside and cytosine, 4-amino-6-oxo-2-vinylpyrimidine nucleoside and guanine, and 4-amino-6-oxo-2-vinylpyrimidine-ethyl-C-nucleoside and uridine.

An mRNA molecule containing at least one (e.g., two, three, or four) electrophilic nucleoside can be generated using methods known in the art or described herein. For example, Example 5 describes the synthesis of 2-amino-6-vinylpurine phosphoramidites which can be incorporated into oligonucleotides as described in Example 6. The oligonucleotides can then be ligated to mRNA molecules to produce templates for translation, or the oligonucleotides can be ligated to fragments of tRNA molecules to form functional linking tRNA molecules, using methods known to one skilled in the art or described herein (see, e.g., Example 7).

Crosslinking between Two Members of a Complementary Crosslinker Pair

Another strategy for linking an mRNA molecule to a linking tRNA involves crosslinking between members of a complementary crosslinker pair (each member being a natural or modified nucleoside) that can react with each other, spontaneously or when an agent or treatment is added. Thus, an mRNA or linking tRNA molecule containing one or more moieties comprising at least one (e.g., two, three, or four) member of the complementary crosslinking pair can be linked to a linking tRNA or mRNA, respectively, containing at least one (e.g., two, three, or four) of the other member of the complementary crosslinking pair. This strategy generally requires that the anticodon of the linking tRNA contains at least one (e.g., two, three, or four) member of the complementary crosslinking pair and corresponds to the codon of the mRNA containing the at least one (e.g., two, three, or four) of the other member of the complementary crosslinking pair. Exemplary complementary crosslinker pairs and their crosslinking reactions are illustrated in FIG. 5.

One approach is to use, as one member of the pair, a modified purine nucleoside containing an olefin at the 2-position of the purine ring. The double bond of the olefin can be selectively attacked by iodine to form an intermediate that could alkylate a thiol group in its proximity. This reaction has been demonstrated to occur in aqueous solution in an intramolecular format. See, Mizutani, M. and Sanemitsu, Y., *J. Org. Chem.* 50:764-768, 1985. The olefin can be synthesized via palladium-catalyzed coupling of 2-iodoadenosine (Nair, V. et al., *J. Chem. Soc., Chem. Commun.* 878-879, 1989; and Nair, V. and Buenger, G. S., *J. Am. Chem. Soc.* 111:8502-8504, 1989), and the resulting nucleoside can then be phosphorylated and ligated to an oligonucleotide to construct an mRNA with the desired modification. Another option is to synthesize 2-iodoadenosine-containing oligonucleotides via solid phase synthesis on CPG resin, and then perform the vinyl coupling while on the CPG resin, before deprotection. This synthesis strategy has been previously used to make 2-alkynyladenosine derivatives (Piton, N. et al., *Nucl. Acids Res.* 35:3128-3143, 2007). A complementary crosslinker pair can include, for example, 2-thiouridine and an adenosine containing an olefin substitution at the 2-position of the purine ring. An mRNA containing an olefin is translated using a translation system containing a linking tRNA with an anticodon including a 2-thiouridine. Crosslinking between the 2-thiouridine and the olefin can be achieved by the addition of iodine, NBS, or ethanethiol and ultraviolet light, which forms an alkyl halide that reacts with the 2-thiouridine.

Other examples of complementary crosslinker pairs include (a) 4-thiouridine and 2-amino-6 vinylpurine, and (b) 4-thiouridine and an adenosine containing a vinyl substituent at the 8-position of the ring. In these cases, crosslinking between the 4-thiouridine and the vinyl group can be achieved by the addition of iodine, NBS, or ethanethiol and ultraviolet light, which forms an alkyl halide that reacts with the 4-thiouridine.

Directly Linking a Polypeptide to an mRNA

In a second approach for linking an mRNA molecule to a polypeptide, the terminus of a functionalized mRNA molecule is directly linked to the polypeptide forming an mRNA-polypeptide complex.

In this approach, the functionalized RNA described herein contains an mRNA, and at the 3' end of the mRNA, a 3' substituent that includes a linking moiety. The linking moiety is capable of entering the aminoacyl-tRNA binding site (A site) of the ribosome during translation of the mRNA, but lacks a peptide bond acceptor moiety that can participate in ribosome catalyzed peptide bond formation. Instead, the linking moiety includes one member of a reactive pair that can react with and become crosslinked to another member of the reactive pair located on the side chain of a linking amino acid of the nascent polypeptide. As used herein, a reactive pair is a pair of moieties that can crosslink with each other to form a covalent bond via a chemical reaction not catalyzed by the ribosome. The crosslinking reaction can occur spontaneously, or by adding an agent or performing a treatment that induces crosslinking A functionalized RNA containing an mRNA and a linking moiety described herein is translated to produce a polypeptide using an in vitro translation system (as described in more detail below) containing an aminoacyl-tRNA containing the linking amino acid. When the linking moiety occupies the A site of the ribosome, its proximity to the P site of the ribosome allows the member of the reactive pair that is part of the linking moiety to react with the other member of the reactive pair that is on the side chain of the linking amino acid that has been incorporated into the growing polypeptide chain and is near the P site. Upon crosslinking between the two members of the reactive pair, the mRNA of the functionalized RNA becomes linked to the polypeptide via the newly created covalent bond between the linking moiety and the linking amino acid.

Functionalized RNAs and Methods of Making and Using them

A functionalized RNA includes an mRNA and one or more non-RNA components. As used herein, an mRNA refers to an RNA comprising a polypeptide coding region and RNA sequences required for translation of the polypeptide. An mRNA can also contain other RNA sequences, such as spacer sequences and primer binding sequences used for PCR amplification of the mRNA. Generally, the functionalized RNA described herein contains, at the 3' end of the mRNA, a 3' substituent containing a linking moiety. In some embodiments, the 3' substituent is made up entirely of the linking moiety, so that the linking moiety is directly attached to the 3' end of the mRNA. In other embodiments, the 3' substituent includes other moieties (e.g., non-RNA molecules) positioned between the linking moiety and the 3' end of the mRNA.

One example of a linking moiety is designed based on the high affinity of the ribosome for the CCA trinucleotide (the structure of which mimics the release factor on stalled ribosomes). The CCA trinucleotide can enter the A site of the ribosome, but cannot participate in ribosome catalyzed peptide bond formation. Thus, the 3' substituent can include a ribo-adenosine derivative having a member of a reactive pair at its 2' or 3' position or a deoxyribo-adenosine derivative having a member of a reactive pair at its 3' position. Preferably, the derivative of a ribo-adenosine or a deoxyribo-adenosine containing a member of a reactive pair is preceded immediately by a CC or dCdC sequence. The adenosine derivative, as exemplified in FIG. 10A, can be a derivative of 2'-deoxy-2'-amino-adenosine (1), 3'-deoxy-3'-amino-adenosine (2), 2'-amino-2'-3'-dideoxy-adenosine (3), or 3'-amino-2'-3'-dideoxy-adenosine (4), each including a member of a reactive pair that is preferably attached at the amino group via a stable covalent bond (e.g., an amide bond).

A linking moiety can also be a derivative of puromycin (see FIG. 10B) that lacks puromycin's peptide bond acceptor moiety (an $NH_2$ group) and contains a member of a reactive pair. Such a puromycin derivative can still bind to the A site of a ribosome, but cannot participate in ribosome-catalyzed bond formation. For example, the peptide bond acceptor moiety of puromycin can be replaced by a member of a reactive pair. An example of a linking moiety that is a derivative of puromycin is N-3'-(2-azido-3-(4-methoxyphenyl) propanamide)-3'-deoxy-$N^6,N^6$-dimethyladenosine. Puromycin derivatives such as 3'-amino-3'-deoxy-$N^6,N^6$-dimethyladenosine (see FIG. 10C), with its peptide bond acceptor moiety removed and containing a member of a reactive pair, can also be used as a linking moiety.

The member of a reactive pair that can be part of the linking moiety could be, for example, an alkyne, an azide, an alkene, a tetrazine, an alpha-halo-benzyl, an alpha-halo-carbonyl, or a photocrosslinker. An alkyne (see FIG. 8A) or an alkene (see FIG. 8B) of any linker length can be used. Azide-reactive moieties can include any azide, for example, an alkyl azide of any linker length (see FIG. 8C). A tetrazine-reactive moiety can include, for example, a 1,2,4,5-tetrazine with an aryl ring or alkyl chain (see FIG. 8D). Alpha-halo-benzyl moieties can include benzyl bromide and benzyl chloride. Examples of alpha-halo-carbonyl moieties include bromoacetate and chloroacetate. Photocrosslinkers (e.g., moieties that can crosslink with other moieties upon activation by light) known in the art can be part of the linking moieties. Examples of photocrosslinkers include psoralen, phenyl azide derivatives, phenyl-diazirine derivatives, benzophenone, and alkyl azides (see FIG. 8E).

Exemplary reactive pairs include (a) an azide and an alkyne; (b) an alkene and a thiol or an amine; (c) a tetrazine and a trans-cyclooctane, a cyclopropene, a bicyclo[2.2.1]hept-2-ene or a norbornene; (d) an α-halo-benzyl and a thiol or an amine; (e) an α-halo-carbonyl and a thiol or an amine; and (f) a photocrosslinker and a moiety that reacts with the photocrosslinker Photocrosslinkers can react non-specifically with many moieties (e.g., alkyl rings and chains, aromatic compounds, heterocycles and alkyl chains containing heteroatoms) on the side chain of an amino acid. In general, it is not critical which member of the reactive pair is part of the linking moiety and which one is part of the linking amino acid.

A functionalized RNA described herein can be generated by reacting an mRNA molecule containing, at its 3' end, a 3' substituent containing (a) a 2' or 3' amino ribo-adenosine, (b) a 3' amino deoxy-ribo-adenosine, or (c) puromycin or derivative thereof, with an acylating agent, such as an N-hydroxysuccinimide (NHS) ester of the reactive moiety. The primary amine group of the adenosine sugar residue, or puromycin or derivative thereof, reacts with the NHS ester to attach, via an amide bond, the reactive moiety to the 3' substituent, thereby forming a linking moiety as part of the 3'substituent. Table 1 lists exemplary acylating agents for adding a reactive moiety to the 3' substituent on a functionalized RNA. An mRNA molecule having at its 3' end a 3' substituent containing a 2' or 3' amino adenosine residue, or puromycin or derivative thereof, can be made using methods known in the art, e.g., Eisenhuth, R. and Richert C., *J. Org. Chem.* (2009) 74, 26-37; Moroder et al., *Angew. Chem. Int. Ed.* (2009) 48, 4056-4060).

The mRNA of the functionalized RNA includes a codon encoding the linking amino acid. This codon is located within the 3' terminal portion of the polypeptide coding region of the mRNA. In some embodiments, the codon encoding the linking amino acid is one of the last three codons of the coding region. In some cases, the codon encoding the linking amino acid is the last or the second to the last codon of the coding region. The codon encoding the linking amino acid can be a sense codon or a non-sense codon (e.g., stop codon). When the codon encoding the linking amino acid is a non-sense codon, the aminoacylated tRNA containing the linking amino acid is an aminoacylated suppressor tRNA (i.e., one that recognizes a non-sense codon).

In some embodiments, the 3' substituent contains only the linking moiety, so the linking moiety is located right at the 3' end of the mRNA. The mRNA can also include a spacer RNA sequence between the last codon of the coding region and the 3' substituent. The spacer sequence can include 1-30 nucleotides, e.g., 1-5, 5-15, 15-20, or 20-25 nucleotides. It may be useful to include a spacer sequence with at least 10 nucleotides, but no more than 300 nucleotides (e.g., 10-200, 50-150, 10-50, 20-100, or 20-50 nucleotides).

TABLE 1

| | |
|---|---|
| Alkyne | an N-hydroxysuccinimide ester of:<br>i) but-3-ynoic acid<br>ii) pent-4-ynoic acid<br>iii) hex-5-ynoic acid<br>iv) hept-6-ynoic acid |
| Azide | an N-hydroxysuccinimide ester of:<br>i) 2-azidoacetic acid<br>ii) 3-azidopropionic acid<br>iii) 4-azidobutyric acid<br>iv) 4-azidopentanoic acid<br>v) 5-azidohexanoic acid<br>vi) 5-azido-2-nitrobenzoic acid |
| Alkene | an N-hydroxysuccinimide ester of:<br>i) but-3-enoic acid<br>ii) pent-4-enoic acid<br>iii) hex-5-enoic acid<br>iv) hept-6-enoic acid |
| Tetrazine | An N-hydroxysuccinimide ester of:<br>i) 2-(4-(1,2,4,5-tetrazin-3-yl)phenyl)acetic acid<br>ii) 2-(4-(1,2,4,5-tetrazin-3-yl)benzylamino)acetic acid<br>iii) 4-(4-(1,2,4,5-tetrazin-3-yl)benzylamino)-4-oxobutanoic acid iv) 2-(6-(pyridin-2-yl)-1,2,4,5-tetrazin-3-yl)methylamino) butanoic acid<br>v) 2((6-(pyridin-2-yl)-1,2,4,5-tetrazin-3-yl)methylamino)acetic acid<br>vi) 4-oxo-4-((6-(pyridin-2-yl)-1,2,4,5-tetrazin-3-yl)methylamino) butanoic acid |
| α-halo-benzyl | an N-hydroxysuccinimide ester of:<br>i) (bromomethyl)benzoic acid<br>ii) (chloromethyl)benzoic acid |
| α-halo-carbonyl | an N-hydroxysuccinimide ester of:<br>i) bromo-acetic acid<br>ii) chloroacetic acid |
| Photo-crosslinker | an N-hydrosuccinimide ester of:<br>i) 4-(7-oxo-7H-furo[3,2-g]chromen-9-yloxy)butanoic acid<br>ii) 4-azido-2,3,5,6-tetrafluorobenzoic acid<br>iii) 4-(3-(trifluoromethyl)-3H-diazirin-3-yl)benzoic acid<br>iv) 4-azido-2-hydroxybenzoic acid<br>v) 3-benzoylbenzoic acid<br>vi) 2-azidoacetic acid<br>vii) 5-azido-2-nitrobenzoic acid |

The 3' substituent of the functionalized RNA can also include a pause moiety that is positioned between the linking moiety and the mRNA. A pause moiety is a moiety that causes the ribosome to stall or pause translation, thereby facilitating linkage of the nascent polypeptide to the linking moiety of the functionalized RNA. When a purified translation system is used to translate the mRNA part of the functionalized RNA, a pause moiety may not be necessary to stall translation, for example, when release factors are omitted from the translation reaction. A pause moiety is generally useful for stalling translation when translation systems based on crude cell lysates are used. Pause moieties are known in the art. For example, a segment of a nucleic acid other than RNA (e.g., DNA) or another polymer, for example locked nucleic acid (LNA), threose nucleic acid (TNA), glycerol nucleic acid (GNA), peptide nucleic acid (PNA), polyethylene glycol (PEG), or a peptide can be ligated to the RNA and employed as a pause moiety. A variety of approaches for attaching such pause moieties to mRNA have been described (see U.S. Pat. Nos. 6,258,558; 6,416,950; and 6,429,300, all incorporated herein by reference). Other types of pause moieties can be used. Certain RNA secondary structures that promote some level of ribosome stalling in natural and artificial genes, and thus play an important role in the regulation of gene expression (e.g., hairpins and pseudoknots), can promote highly effective stalling. A variety of hairpin and pseudoknot structures described in the literature can be inserted near the 3' end of a coding RNA to effect stalling (Tate, W. P. and Brown, C. M. (1992) *Biochemistry* 31:2443-2450; Young, J. C. and Andrews, D. W. (1996) *EMBO J.* 15:172-181; Kozak, M. (2001) *Nucl. Acids Res.* 29:5226-5232; Kontos, H., Napthine, S., and Brierley, I. (2001) *Mol. Cell. Biol.* 21:8657-8670; Plant, E. P. and Dinman, J. D. (2005) *Nucl. Acids Res.* 33:1825-1833; Yanofsky, C. (2007) *RNA* 13:1141-1154, and references cited therein, all of which are incorporated herein by reference).

The functionalized RNA described herein can be used to link a polypeptide encoded by the mRNA of the functionalized RNA to the mRNA through the 3' substituent, and thereby generate an mRNA-polypeptide complex. The mRNA of the functionalized RNA is translated to produce a polypeptide using an in vitro translation system that includes an aminoacyl-tRNA comprising the linking amino acid. The linking amino acid has a side chain that contains a member of a reactive pair that can crosslink with the member of the reactive pair in the linking moiety. Non-limiting linking amino acids that can be used in these methods include the D or L, D- or L-N-methyl, and D- or L-N-alkyl versions of: (a) β-azidoalanine; (b) azidohomoalanine; (c) azidonorvaline; (d) 4-ethynyl-phenylalanine; (e) 2-amino-hex-5-ynoic acid; (f) trans-4,5-dehydro-lysine; (g) cysteine; (h) lysine; (i) allylglycine; (j) propargylglycine; (k) 2,3-diaminopropionic acid; (l) vinylglycine; (m) p-azido-phenylalanine; (n) S-allyl-cysteine; (o) S-(2-amino ethyl)-cysteine; (p) ornithine; (q) 2-amino-3-cycloallylpropanoic acid; (r) 2-amino-2-(trans-cyclooct-4-enyl) acetic acid; and (s) 2-amino-2-(trans-cy-clooct-3-enyl) acetic acid.

Crosslinking between members of a reactive pair occurs when the linking moiety occupies the A site of the ribosome. In some cases, the crosslinking step requires the addition of an agent or a treatment. For example, copper ion can be added to promote crosslinking between an alkyne and an azide. The translation system can be treated with light and ethanethiol or β-mercaptoethanol to activate crosslinking between an alkene and a thiol or an amine. Aqueous iodine or bromine can also be used to promote crosslinking between an alkene and a thiol. When a photocrosslinker is involved, light, e.g., UV light, is used to activate the crosslinking reaction. The agent or treatment is added at a time when the ribosome has completed translation of the functionalized RNA and has stalled, and the functionalized RNA and ribosome have been incubated for a sufficient amount of time to permit the linking moiety of the 3' substituent to occupy the A site of the ribosome. It can take anywhere between 30 minutes to 24 hours or more after starting translation to provide sufficient time for the linking moiety to occupy the A site. A high potassium and magnesium wash step could be carried out to improve occupancy of the A site by the linking moiety. The optimal interval for allowing the in vitro translation reaction to proceed before adding the agent or treatment to promote crosslinking can be determined by assaying the yield of crosslinked mRNA-polypeptide complexes, e.g., by electrophoresis.

The methods described herein generate novel mRNA-polypeptide complexes. The mRNA-polypeptide complexes may include any non-RNA components of the functionalized RNAs used to generate the mRNA-polypeptide complexes. The functionalized RNAs and the polypeptides in the complexes are linked via various bridging groups, depending on what reactive pairs are involved. For example, the mRNA and polypeptide may be linked through a bridging group selected from the group of: a triazole, a thioether, a secondary amine, a pyridazine, a 3,4-diazanorcaradiene, benzylthioether, and a benzylamine. A "bridging group" as used herein is the residue formed by the reaction between the two members of a reactive pair. Table 2 is a non-exhaustive list of the various types of bridging groups created between the functionalized RNA and the polypeptide by using different reactive pairs. Also see FIGS. 9A-C for examples of the bridging groups created between a functionalized RNA and a polypeptide using the methods described herein.

Provided herein are libraries of any of the functionalized RNAs and the mRNA-polypeptide complexes described herein. In some embodiments of these libraries, the mRNA in each complex encodes a different protein or each mRNA in each mRNA-polypeptide complex encodes a different protein. Some embodiments of these libraries contain a plurality of different mRNA-polypeptide complexes. As described in detail below, libraries of functionalized RNAs may be used to generate a library of mRNA-polypeptide complexes, that may in turn be used to screen for polypeptides that interact with (e.g., specifically bind) a target.

Also provided are translation systems that contain any of the libraries of functionalized RNAs described herein and at least one aminoacylated tRNA containing any of the linking amino acids described herein. In some embodiments of these translation systems, the aminoacylated tRNA is an aminoacylated suppressor tRNA.

TABLE 2

| Reactive Pair | Bridging Groups Formed Between Functionalized RNA and Polypeptide |
|---|---|
| an azide and an alkyne | Triazole |
| an alkene and a thiol | Thioether |
| an alkene and an amine | secondary amine |
| a tetrazine and a trans-cyclooctane | Pyridazine |
| a tetrazine and a cyclopropene | 3,4-diazanorcaradiene |
| a tetrazine and a bicyclo[2.2.1]hept-2-ene | Pyridazine |
| a tetrazine and a norbornene | Pyridazine |
| an α-halo-benzyl and a thiol | Benzylthio ether |
| an α-halo-benzyl and an amine | Benzylamine |
| an α-halo-carbonyl and a thiol | Thioether |
| an α-halo-carbonyl and an amine | secondary amine |

Methods of Making and Using Libraries

The methods described herein for linking an mRNA to a polypeptide encoded by the mRNA through a linking amino acid and a linking moiety and for linking an mRNA to a polypeptide encoded by the mRNA through a linking tRNA can be used to create libraries of polypeptides and to select novel polypeptides that have specific target-binding or other activities. Accordingly, provided herein are methods of selecting for a polypeptide (or an mRNA encoding a polypeptide) that interacts with a target or exhibits another desired, specific activity. Also provided herein are methods of using libraries of the mRNA-polypeptide and the mRNA-tRNA-polypeptide complexes described herein to optimize the binding or functional properties of a polypeptide. A library will generally contain at least $10^2$ members, more preferably at least $10^6$ members, and more preferably at least $10^9$ members (e.g., any of the mRNA-polypeptide complexes and/or mRNA-tRNA-polypeptide complexes described herein). In some embodiments, the library will include at least $10^{12}$ members or at least $10^{14}$ members. In general, the members will differ from each other; however, it is expected there will be some degree of redundancy in any library. The library can exist as a single mixture of all members, or can be divided into several pools held in separate containers or wells, each containing a subset of the library, or the library can be a collection of containers or wells on a plate, each container or well containing just one or a few members of the library.

A library of mRNAs, each mRNA comprising a member of a reactive pair that can participate in crosslinking (often referred to as a functionalized RNA) to an appropriately modified polypeptide or tRNA. Each mRNA in the library preferably comprises a translation initiation sequence, a start codon, and a variable polypeptide (e.g., protein or short peptide) coding region that is generated by, for example, a random or semi-random assembly of nucleotides, and varies from mRNA to mRNA in the library (though there will likely be some degree of redundancy within the library). The translation initiation sequence, start codon, and variable polypeptide coding region can be flanked by known, fixed sequences that can be used for PCR amplification of the mRNA, e.g., after selection. Other fixed sequences that can be present include those corresponding to restriction enzyme recognition sequences as well as sequences that encode amino acids that can participate in chemical or enzymatic cross-linking reactions, such that the polypeptide produced can be modified or derivatized after translation, or that encode a fixed C-terminal extension.

Once a library of functionalized RNAs of the invention is generated, the mRNAs present in the members of the library can be translated. The resulting polypeptides (e.g., displayed polypeptides) will be linked to their corresponding functionalized RNAs as described herein (e.g., as an mRNA-polypeptide complex or an mRNA-tRNA-polypeptide complex). Translation is carried out using a translation system containing a set of aminoacyl-tRNAs that includes the appropriate linking tRNA or linking amino acid matched to the linking moiety utilized in the functionalized RNAs in the library. Aminoacyl-tRNAs containing linking amino acids, other unnatural amino acids, or natural amino acids can be generated using methods known in the art and described herein. When employing a linking amino acid, the linking amino acid can be attached to the tRNA via an ester bond or a stable, non-hydrolyzable covalent bond (e.g., an amide bond) (see Fraser, T. H. and Rich, A., (1973) *Proc. Natl. Acad. Sci. USA* 70:2671-2675; Merryman, C. et al. (2002) *Chemistry and Biology* 9:741-746; U.S. Pat. No. 6,962,781). Other aminoacyl-tRNAs that may be used include those with the linking amino acids attached via a stable 3' hydrazide, oxyamide, methylene, or oxymethylene linkage. When employing a linking tRNA, the amino acid attached to the linking tRNA is preferably attached via a stable, non-hydrolyzable covalent bond.

Numerous in vitro translation systems have been described in the literature. The most common systems utilize rabbit reticulocyte lysates, wheat germ extracts, or *E. coli* extracts, which are available from a number of commercial sources in kit form (e.g., Ambion, Austin, Tex.; Promega, Madison, Wis.; Novagen/EMD Chemicals, Gibbstown, N.J.; Qiagen, Valencia, Calif.). Other systems based on purified translation factors and ribosomes have been described (Shimizu, Y. et al. (2001) *Nat. Biotech.* 19:751-755; Josephson, K., Hartman, M. C. T., and Szostak, J. W. (2005) *J. Am. Chem. Soc.* 127: 11727-11735; Forster, A. C. et al. (2003) *Proc. Natl. Acad. Sci. USA* 100: 6353-6357). A system based on purified *E. coli* translation factors is commercially available (PURExpress™; New England Biolabs, Ipswich, Mass.). In general, the conditions recommended by the kit manufacturers are suitable for in vitro translation of the mRNA portion of the functionalized RNAs described herein. The optimal interval for allowing the in vitro translation reaction to proceed can be determined by assaying the yield of crosslinked mRNA-polypeptide complexes or mRNA-tRNA-polypeptide complexes, e.g., by electrophoresis.

As described above, the crosslinking reaction between members of the reactive pair occurs after translation has been completed and the ribosome has stalled, and the linking moiety has occupied the A site of the ribosome. In some embodiments, one or more additional agents or treatments are required, e.g., after translation, to induce crosslinking. The aminoacyl-tRNA containing the linking tRNA or the linking amino acid may recognize a sense codon or a non-sense (stop) codon. In some embodiments, the linking tRNA or the tRNA attached to the linking amino acid recognizes a sense codon that immediately precedes one or two stop codons on the functionalized RNA. In some embodiments, the tRNA recognizes a stop codon (i.e., is a suppressor tRNA) on the functionalized RNA. It may be advantageous to use a purified in vitro translation system lacking release factors (e.g., Tan, Z. et al. (2005). *Methods* 36:279-290; and U.S. Pat. No. 6,977,150). The absence of release factors will prevent premature dissociation of the peptidyl tRNA from the ribosome. The absence of release factors is especially useful if crosslinking depends on the addition of an agent or the use of ultraviolet light to initiate the crosslinking reaction.

Translation can be performed with naturally-occurring amino acids (i.e., the 20 natural proteinogenic amino acids commonly found in natural proteins). The 20 natural proteinogenic amino acids are alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Alternatively, "unnatural" amino acids, which have side chains not present in the 20 naturally-occurring amino acids listed above, can be used. Unnatural amino acids include, but are not limited to: S-(2-aminoethyl)-L-cysteine, 4-fluoro-L-tryptophan, L-β-azidohomoalanine, β-hydroxy-L-norvaline, 4,4-difluoro-L-glutamate, 5'5'5'-trifluoro-L-leucine, L-2-amino-hex-5-ynoic acid, L-canavanine, 3-fluoro-L-valine, 2-fluoro-L-phenylalanine, 4-fluoro-L-phenylalanine, 4-chloro-L-phenylalanine, O-methyl-L-tyrosine, 4-pyridinepropanioc acid, 2-amino-2-(1H-tetrazol-5-yl) acetic acid, 5-fluoro-L-tryptophan, L-t-butyl glycine, 4-fluoro-L-glutamate, 7-aza-L-tryptophan, trans-4,5-dehydro-L-lysine, O-methyl-L-threonine, L-norleucine, 2-amino-3-methoxybutanoic acid, L-ethionine, L-glutamic acid-γ-methyl ester, 3,4-dehydro-L-proline, L-crotylglycine, 1-amino cyclopentanecarboxylic acid, L-threo-β-hydroxy aspartic acid, 1-aminocyclohexane-1-carboxylic acid, quisqualic acid, 4-thia-L-isoleucine, β-t-butyl-L-alanine, 3-fluoro-L-tyrosine, thiazolidine-2-carboxylic acid, α-methyl-L-aspartic acid, L-norvaline, α-methyl-L-proline, L-thiazolidine-4-carboxylic acid, L-azetidine-2-carboxylic acid, β-methyl-L-phenylalanine, 5-hydroxy-L-tryptophan, 3-(thianaphthen-3-yl)-L-alanine, ibotenic acid, 4-methyl-L-glutamate, 4-aza-L-leucine, 3-(2-thienyl)-L-alanine, L-β-(1,2,4-triazol-3-ylalanine, L-phenylglycine, L-allylglycine, p-nitro-L-phenylalanine, L-p-iodo-phenylalanine, N-methyl-L-aspartate, N-methyl-L-leucine, alpha-hydroxy amino acids, N-methyl amino acids, N-alkyl amino acids, alpha-alkyl amino acids, beta-amino acids, D-amino acids, and other unnatural amino acids known in the art. (See, e.g., Josephson et al., (2005) *J. Am. Chem. Soc.* 127: 11727-11735; Forster, A. C. et al. (2003) *Proc. Natl. Acad. Sci. USA* 100: 6353-6357; Subtelny et al., (2008) *J. Am. Chem. Soc.* 130: 6131-6136; Hartman, M. C. T. et al. (2007) *PLoS ONE* 2:e972; and Hartman et al., (2006) *Proc. Natl. Acad. Sci. USA* 103:4356-4361). Essentially any amino acid that, when attached to an appropriate tRNA, can be assembled into a polymer by natural or mutant ribosomes can be used (see Sando, S. et al., (2007) *J. Am. Chem. Soc.* 129:6180-6186; Dedkova, L. et al. (2003) *J. Am. Chem. Soc.* 125: 6616-6617; Josephson, K., Hartman, M. C. T., and Szostak, J. W. (2005) *J. Am. Chem. Soc.* 127:11727-11735; Forster, A. C. et al. (2003) *Proc. Natl. Acad. Sci. USA* 100:6353-6357; Subtelny, A. O., Hartman, M. C. T., and Szostak, J. W. (2008) *J. Am. Chem. Soc.* 130:6131-6136; and Hartman, M. C. T. et al. (2007) *PLoS ONE* 2:e972).

When unnatural amino acids are desired, it may be advantageous to use a purified translation system that lacks endogenous aminoacylated tRNAs (Shimizu, Y. et al. (2001) *Nat. Biotech.* 19:751-755; Josephson, K., Hartman, M. C. T., and Szostak, J. W. (2005) *J. Am. Chem. Soc.* 127: 11727-11735; Forster, A. C. et al. (2003) *Proc. Natl. Acad. Sci. USA* 100: 6353-6357). If unnatural amino acids are used with an in vitro translation system based on a lysate or extract, it may be desirable to deplete the extract of endogenous tRNAs, as previously described (see Jackson, R. J., Napthine, S., and Brierley, I. (2001) *RNA* 7:765-773).

When using natural amino acids with an in vitro translation system based on a lysate or extract, translation is dependent on the enzymatic charging of amino acids onto tRNAs by tRNA synthetases, all of which are components of the extracts. Alternatively, in vitro translation systems that use purified translation factors and ribosomes, or tRNA-depleted extracts, require that aminoacylated tRNAs be provided. In these instances, purified or in vitro synthesized tRNAs can be charged with amino acids using chemical (see Frankel, A., Millward, S. W., and Roberts, R. W. (2003) *Chem. Biol.* 10:1043-1050) or enzymatic procedures (Josephson, K., Hartman, M. C. T., and Szostak, J. W. (2005) *J. Am. Chem. Soc.* 127: 11727-11735; Murakami, H. et al. (2006) *Nat. Methods* 3:357-359).

Numerous publications describe the recovery of mRNA-displayed polypeptides from translation complexes, and these are suitable for use with the methods described herein (Liu, R. et al. (2000). *Methods Enzymol.* 318:268-293; Baggio, R. et al. (2002). *J. Mol. Recognit.* 15:126-134; U.S. Pat. No. 6,261,804). The recovery of mRNA-displayed polypeptides may be facilitated by the use of various "tags" that are included in the polypeptide by translation of fixed sequences of the polypeptide coding sequence and which bind to specific substrates or molecules. Numerous reagents for capturing such tags are commercially available, including reagents for capturing the His-tag, FLAG-tag, glutathione-S-transferase (GST) tag, strep-tag, HSV-tag, T7-tag, S-tag, DsbA-tag, DsbC-tag, Nus-tag, myc-tag, hemagglutinin (HA)-tag, or Trx-tag (Novagen, Gibbstown, N.J.; Pierce, Rockford, Ill.). mRNA-displayed peptides can also be isolated by binding of a polyA tail on the mRNA to polydT resin, or a combination of a polyA tail and a His-tag.

After in vitro translation, the displayed polypeptides can be post-translationally modified to improve or alter their properties. One way to accomplish this is by incorporating unnatural amino acids with reactive side chains into the polypeptides that make up the library. After translation, the newly formed polypeptides can be reacted with molecules that react specifically with the reactive side chain of the incorporated amino acid. For example, an amino acid with a terminal alkyne side chain can be incorporated into the polypeptide library and subsequently reacted with an azido sugar, creating a library of displayed polypeptides with sugars attached at the positions of the alkynyl side chains (Josephson, K., Hartman, M. C. T., and Szostak, J. W. (2005) *J. Am. Chem. Soc.* 127: 11727-11735). A variety of reactive side chains can be used for such post-translational conjugation, including amines, carboxyl groups, azides, terminal alkynes, alkenes, and thiols.

One particularly useful modification is based on the cross-linking of amino acids to produce cyclic structures. Cyclic regions in a protein contain a rigid domain which reduces conformational flexibility and degrees of rotational freedom, leading to very high affinity binding to target proteins. A number of methods for cyclizing a polypeptide are available to those skilled in the art and are incorporated herein by reference. Typically, the chemical reactivity of specific amino acid side chains and/or the carboxyl or amino termini of the polypeptide are exploited to crosslink two sites of the polypeptide to produce a cyclic molecule. In one method, the thiol groups of two cysteine residues are cross-linked by reaction with dibromoxylene (see Timmerman, P. et al., (2005) *ChemBioChem* 6:821-824). Tri- and tetrabromoxylene can be used to produce polypeptides with two and three loops, respectively. In another exemplary method, a side chain amino group and a terminal amino group are cross-linked with disuccinimidyl glutarate (see Millward, S. W. et al., *J. Am. Chem. Soc.* 127:14142-14143, 2005). In other approaches, cyclization is accomplished by making a thioether bridging group between two sites on the polypeptide. One chemical method relies on the incorporation of an N-chloroacetyl modified amino acid at the N-terminus of the polypeptide, followed by spontaneous reaction with the thiol side chain of an internal cysteine residue (see Goto, Y. et al. (2008) *ACS Chem. Biol.* 3:120-129). An enzymatic method relies on the reaction between (1) a cysteine and (2) a dehydroalanine or dehydrobutyrine group, catalyzed by a lantibiotic synthetase, to create the thioether bridging group (see Levengood, M. R. and Van der Donk, W. A., *Bioorg. and Med. Chem. Lett.* 18:3025-3028, 2008).

After the in vitro translation reaction has been performed, and prior to the selection step, the mRNA portion of the functionalized RNA is typically reversed-transcribed to produce a RNA-DNA hybrid molecule (i.e., a cDNA). This serves to protect the RNA from degradation, and also prevents the RNA from folding into a secondary structure that could bind to the selection target, which would lead to selection of inappropriate products (i.e., the selection of RNA aptamers rather than polypeptide aptamers).

A library of mRNA-polypeptide complexes or mRNA-tRNA-polypeptide complexes (also referred to herein as an mRNA display library) generated using the above described methods, and which may or not have been subjected to a post-translational modification (such as cyclization of the polypeptide, as described above), can be subjected to a batch selection step to isolate those complexes displaying desirable polypeptides. A target used in the selection step is typically isolated by purification from a natural biological source or from a recombinant DNA expression system. Alternatively, the target may be used in a non-purified state or may be prepared by chemical synthesis. The target may be a protein, such as a cell-surface receptor (for example, a cytokine or neurotransmitter receptor), an enzyme, a transcription factor, a hormone, a cytokine, an antibody, an antibody domain, an ion channel, a chaperone, an adhesion molecule, or any other nuclear, cytoplasmic, cell-surface, or serum protein, or a fragment of such a protein. The target may also be a lipoprotein, polysaccharide, glycoprotein, proteoglycan, peptidoglycan, lipid, small molecule, RNA, DNA, or any other nucleic acid molecule. The target may be any substance or structure for which it is desirable to isolate a binding polypeptide.

Typically, a purified target (e.g., a protein or any of the target molecules described herein) is conjugated to a solid substrate, such as an agarose or synthetic polymer bead. The conjugated beads are mixed with the mRNA display library and incubated under conditions (e.g., temperature, ionic strength, divalent cations, and competing binding molecules) that permit specific members of the library to bind the target. Alternatively, the purified target protein can be free in solution and, after binding to an appropriate polypeptide, the mRNA-polypeptide complex or the mRNA-tRNA-polypeptide complex with a bound target is captured by an antibody that recognizes the target (e.g., target protein) at a site distinct from the site where the displayed polypeptide binds. The antibody itself can be bound to a bead, or it may be subsequently captured by a suitable substrate, such as Protein A or Protein G resins. The binding conditions can be varied in order to change the stringency of the selection. For example, low concentrations of a competitive binding agent can be added to ensure that the selected polypeptides have a relatively higher affinity. Alternatively, the incubation period can be chosen to be very brief, such that only polypeptides with high $k_{on}$ rates will be isolated. In this manner, the incubation conditions play an important role in determining the properties of the selected polypeptides. Negative selections can also be employed. In this case, a selection to remove polypeptides with affinity to the substrate to which the target is bound (e.g., Sepharose) is carried out by applying the displayed library to substrate beads lacking the target protein. This step can remove mRNAs and their encoded polypeptides that are not specific for the target protein. Numerous references describing how to conduct selection experiments are available. (See, e.g., U.S. Pat. No. 6,258,558; Smith, G. P. and Petrenko, V. A., (1997) Chem. Rev. 97:391-410; Keefe, A. D. and Szostak, J. W. (2001) Nature 15:715-718; Baggio, R. et al. (2002) J. Mol. Recog. 15:126-134; Sergeeva, A. et al. (2006) Adv. Drug Deliv. Rev. 58:1622-1654).

The frequency at which binding molecules are present in a library of random sequences is expected to be very low. Thus, in the initial selection step, very few polypeptides meeting the selection criteria (and their associated mRNAs) are expected to be recovered. Typically, the selection is repeated with mRNAs selected from the first round of selection. This is accomplished by using PCR to amplify the mRNAs or corresponding cDNAs selected in the first round, followed by in vitro transcription to produce a new library of mRNAs. PCR primers corresponding to the 5' and 3' ends of the mRNAs in the library are used. Typically, the 5' primer will extend in the 5' direction beyond the end of the mRNA so that a bacterial promoter, such as a T7 promoter, is added to the 5' end of each amplified molecule. Once amplified, the double-stranded DNA can be used in an in vitro transcription reaction to generate the mRNA for a second round of selection. This mRNA is modified as necessary, e.g., by incorporating it into functionalized RNA as described above.

The selection process typically involves a number of rounds or cycles, in which the pool of selected molecules is incrementally enriched in a specific set of sequences at the end of each round. The selection conditions may be the same for each round, or the conditions may change, for example, in order to increase the stringency of selection in later rounds. The progress of selection may be monitored by the use of isotopically-labeled amino acids, such as $^{35}S$ methionine. The amount of radiolabeled polypeptide bound to the target at each round is measured, and a progressive increase in recovered radiolabel is indicative of a progressive enrichment in RNA molecules encoding polypeptides with binding affinity to the target. After any round, the PCR products may be cloned and sequenced. Generally, cloning and sequencing is performed after a round in which appreciable (>5%) amounts of radiolabeled polypeptide are recovered in the target-bound pool. Sequences that are found in multiple isolates are candidates for encoding polypeptides that bind specifically to the target. Alternatively, high throughput sequencing of thousands of clones can be performed after early rounds, such as after the third and fourth round. Sequences that increase in frequency between the third and fourth rounds are candidates for encoding polypeptides that bind specifically to the target. The polypeptide encoded by any sequence may be expressed or synthesized and tested for binding affinity to the original target protein used in the selection.

The libraries and methods of the present invention may be used to optimize the function or properties of a polypeptide. In one approach, mutagenic PCR (Keefe, A. D. and Szostak, J. W. (2001). Nature 15:715-718) is used to introduce sequence variation in the library once the population is enriched in polypeptides with a certain level of binding affinity. Alternatively, a single RNA sequence encoding a polypeptide with defined binding properties can be replicated but with a defined level of mutations, or mutagenic PCR can be performed to produce a pool of mutant molecules. The resulting mixture of mRNA molecules produced from such a pool is expected to encode polypeptides with a range of improved, similar, or reduced affinities as compared to the starting sequence, and a selection performed on mRNAs from such a pool may be expected to identify polypeptides with improved affinity if an appropriate stringency regimen is used during the selection.

In a second approach, optimization is performed in a directed manner. A sequence encoding a polypeptide with established binding or functional properties is subjected to site-directed mutagenesis, whereby a series of sequences is produced, with each sequence having one codon replaced with, for example, an alanine codon. The number of sequences in the set is equal to the number of amino acid residues that are to be mutated. The polypeptide product of each "alanine scanning" mutant is tested for binding or functional properties. Sites at which an alanine substitution affects the binding or function of the polypeptide are considered critical residues. Alternatively, the sequences can be pooled, subjected to one or more rounds of a high stringency selection, and a pool of sequences representing high affinity binding polypeptides is isolated. Critical residues are identified as those that cannot be substituted by an alanine residue without loss of activity. Once the critical residues are identified, a pool of mRNA molecules encoding a wide variety of natural (or unnatural) amino acids at each critical position is produced. The resulting pool is subjected to one or more rounds of a high stringency selection (with the appropriate mixture of tRNAs charged with natural or unnatural amino acids), and sequences representing high affinity binding polypeptides are isolated. In this manner, an optimal polypeptide can be identified. Since the optimal sequence may not necessarily be identified by combining optimal residues at individual sites, it is useful to test mutations at multiple sites in combination.

EXAMPLES

Example 1

Synthesis of Bifunctional Crosslinker N,N'-bis-bromoacetyl-1,2-diaminobenzene 1,2-phenylenediamine (2.75 g, 25 mmoles) was dissolved in 100 mL of dry tetrahydrofuran (THF) containing triethylamine (8.71 mL, 62.5 mmoles) and cooled in an ice bath. A solution of bromoacetylbromide in THF (50 mmoles, 4.35 mL in 15 mL THF) was added slowly and the resulting solution is stirred at 0° C. for 1 hour followed by an additional 3 hours at room temperature. Water (25 mL) was then added and the solution allowed to stand until a precipitate formed. The precipitate comprising N,N'-bis-bromoacetyl-1,2-diaminobenzene was filtered off and re-crystallized from hot methanol.

Donor oligonucleotide containing a $^{4S}U$ residue was purchased as TOM-protected RNA from the Keck oligonucleotide facility at Yale University (New Haven, Conn.). The lyophilized powder was dissolved in 0.1 mL of DMSO. Once fully dissolved, triethylamine trihydrofluoride (0.125 mL; neat) was added and the solution incubated at 65° C. for 2 hours. The deprotected RNA was precipitated with butanol, washed once with absolute cold ethanol and once with 70% ethanol/water.

The pellet was dissolved in 0.1 mL of diethylpyrocarbonate (DEPC)-treated water and 10 µL were purified by ion exchange HPLC on a Dionex DNA-pac column using a gradient of 0.01 M NaCl to 1 M NaCl containing EDTA in nuclease free water. The major fraction was collected and desalted in an OPC purification cartridge (ABI; Carlsbad, Calif.), using the conditions recommended by the manufacturer. 1.5 nmole of the donor oligonucleotide was obtained and HPLC with high resolution mass spectroscopy was used to confirm the presence of the thiouridine residue.

In order to activate the $^{4S}U$ oligonucleotide for crosslinking, 1.5 nmoles of donor oligonucleotide (25 µL of a 83 µM solution) was dissolved in 70 µL of 0.1 M $K_2HPO_4/KH_2PO_4$ pH: 8.0. A solution of the electrophile N,N-bis-bromoacetyl-1,2-diaminobenzene was prepared (1 mg in 30 µL of dimethylformamide (DMF)) and added to the $^{4S}U$ oligonucleotide. The sample was allowed to sit at room temperature for 1.5 hours and the reaction terminated by passing the sample through a micro-biospin 6 column (Bio-Rad; Hercules, Calif.) and precipitated with 1 mL of butanol. The oligo was washed once with ethanol, centrifugated, and evaporated to dryness on a Speed-Vac™ lyophilizer.

The activated oligonucleotide is ligated onto the end of an mRNA preparation containing the sequences of interest by splint ligation, in which the mRNA and activated oligonucleotide are annealed to a DNA oligonucleotide containing sequences complementary to both the mRNA and the activated oligonucleotide and are joined together using T4 DNA ligase (Das, S. R. and Piccirilli, J. A., *Nat. Chem. Biol.* 1:45-52, 2005). The resulting mRNA is then subjected to in vitro translation and tRNA crosslinking.

Example 2

Preparation of Furan Modified Oligonucleotides from 2'-amino Uridine (or Cytidine) Containing Oligonucleotides Oligonucleotides containing a single 2'-amino nucleoside moiety are synthesized via solid phase synthesis using TOM-protected RNA amidites (Glen Research; Sterling, Va.) and 2'-amino uridine CED phosphoramidite (Chemgenes; Wilmington, Mass.) on an Expedite™ (Millipore; Billerica, Mass.) RNA synthesizer using the conditions recommended by the manufacturers.

2-furyl propionic acid is synthesized as described by Halila et al. (*Chem. Commun.* 21:936-938, 2005) from commercially available 3-(2-furyl)acrylic acid. 2-furyl propionic acid (2 g, 14.3 mmoles) is dissolved in anhydrous tetrahydrofuran (50 mL) followed by addition of triethylamine (2 molar equivalents) and cooled to 0° C. N-hydroxysuccinimide (1.1 molar equivalent) is then added followed by solid dicyclohexylcarbodiimide (1.1 molar equivalent), which is added in portions during a period of 30 minutes. Once the addition is complete the reaction is allowed to reach room temperature and stirred overnight. The volatiles ware evaporated and the reaction diluted with dichloromethane (10 mL). The product is passed through a short column packed with silica gel and eluted with dichloromethane. The solvent is evaporated to obtain the desired compound.

The crude oligonucleotide (250 µmoles) containing 2'-amino uridine is dissolved in 100 µL of 70 mM boric acid (pH 8.5) and cooled on an ice-bath. Formamide (60 µL) is added, followed by addition of a freshly prepared solution of NHS-furan (15 molar equivalents) in DMF (40 µL) (Handbook of RNA Biochemistry; Hartmann, R. K., Biendereif, A., Schon, A., and Westhof, E., 2005). A similar procedure can be used for isocyanate- and isothiocyanate-activated furan derivatives.

The resulting solution is incubated for 60 minutes on ice and a second aliquot of NHS-furan ester is added and incubated for an additional hour. The solution is extracted twice with chloroform (300 µL) at room temperature and precipitated by addition of 20 µL of 3 M sodium acetate and 1.3 mL ethanol. The mixture is cooled to –70° C. for 1 hour and the precipitated oligonucleotide pelleted by centrifugation. The oligonucleotide is washed once with 70% ethanol, centrifuged, and evaporated to dryness using a Speed-Vac™ lyophilizer. The oligonucleotide is purified by preparative reverse phase HPLC on a C-18 column using a linear gradient of triethylammonium acetate (20 mM) to 60% acetonitrile in triethylammonium acetate (20 mM). Fractions containing the oligonucletide are lyophilized to dryness.

The furan-modified oligonucleotide is ligated onto the end of an mRNA preparation containing the sequences of interest by splint ligation, in which the mRNA and activated oligonucleotide are annealed to a DNA oligonucleotide containing sequences complementary to both the mRNA and the activated oligonucleotide and are joined together using T4 DNA ligase (New England BioLabs, Ipswich, Mass.). The resulting mRNA is then subjected to in vitro translation and tRNA crosslinking.

Example 3

Preparation of Furan-modified Oligonucleotides from 2'-amino Furan Modified Phosphoramidite 2'-amino furan-modified phosphramidite [2'-deoxy-2'-(2-furyl-2-ethoxycarbonylamino)-5'-O-(4,4'-dimethoxytrityl) uridine 3'-(2-cyanoethyl N,N-diisopropylphosphoramidite)] is prepared from its 2'-amino nucleoside as described previously (Halila et al., 2005, supra). RNA oligonucleotides containing the 2'-amino furan moiety are synthesized via solid phase synthesis using TOM-protected RNA phorphoramidites (Glen Research; Sterling, Va.) and 2'-amino uridine CED phosphoramidite (Chemgenes; Wilmington, Mass.) on an Expedite (Millipore; Billerica, Mass.) RNA synthesizer using the conditions recommended by the manufacturers. The desalted oligonucletide is purified by denaturing PAGE electrophoresis (15% urea) and further purified via RP-HPLC on a C-18 column using a linear gradient of triethylammonium acetate (20 mM) to 60% acetonitrile in triethylammonium acetate (20 mM). Fractions containing the desired oligonucleotide are lyophilized to dryness.

Example 4

Crosslinking of an mRNA to a tRNA Via a 4-oxo-2-pentenal Moiety

An mRNA containing a 2'-amino furan modification is incubated with an in vitro translation reaction mixture at 37° C. After 30 min 4-oxo-2-pentenal is formed by adding 1 molar equivalent (with respect to mRNA) of N-bromosuccinimide, freshly prepared in phosphate buffer containing 10 mM NaCl, pH 7. The crosslinking reaction of the 4-oxo-2-pentenal mRNA is allowed to proceed for 8 hours.

Example 5

Preparation of 2-amino-6 Vinylpurine Phosphoramidite

The 2-amino-6-vinylpurine phosphoramidite 2-acetamido-5'-O-DMT-2'-O-TOM-3'-cyanoethyl diisopropylphospharamidite-9-D-ribofuranosyl-6-(2-(phenylthio)ethyl)purine (shown as compound (1) in FIG. 6) is synthesized as described below. 2-amino-9-(2,3,5-tri-O-tert-butyldimethylsilyl-D-ribofuranosyl)-6-vinylpurine (shown as compound (2) in FIG. 6) is synthesized as described by Nagatsugi et al. (*Nucleic Acids Symp. Ser.* 67-68, 1997). 0.22 g (2 mmoles) of thiophenol is added to a 40 mL solution of 1.27 g (2 mmoles) of 2-amino-9-(2,3,5-tri-O-tert-butyldimethylsilyl-D-ribofuranosyl)-6-vinylpurine in 20% dichloromethane in ethanol and the resulting solution stirred at room temperature for 1 hour. The product, 2-amino-9-(2,3,5-tri-O-tert-butyldimethylsilyl-D-ribofuranosyl)-6-(2-(phenylthio)ethyl)purine (shown as compound (3) in FIG. 6), is purified by silica gel chromatography using chloroform/methanol (99:1).

The 2-amino group of 2-amino-9-(2,3,5-tri-O-tert-butyldimethylsilyl-D-ribofuranosyl)-6-(2-(phenylthio)ethyl) purine is protected by amidation to produce 2-acetamido-9-(2,3,5-tri-O-tert-butyldimethylsilyl-D-ribofuranosyl)-6-(2-(phenylthio)ethyl)purine (shown as compound (4) in FIG. 6). To produce compound (4) (in FIG. 6), a solution of 1.33 g (1.7 mmoles) of compound (3) (in FIG. 6) in pyridine (50 mL) is cooled to 0° C. and 1.5 molar equivalents acetyl chloride is added. The solution is allowed to reach room temperature and stirred for 2 hours. Water (5 mL) is added to quench the unreacted acylating agent and the solution stirred for additional 10 minutes. Volatiles are evaporated under reduced pressure and the residue dissolved in chloroform (75 mL) and washed twice with a saturated solution of sodium bicarbonate (2×50 mL), water (50 mL), and brine (50 mL). The organics are dried with magnesium sulfate, filtered, and evaporated under reduced pressure to yield compound (4) (in FIG. 6).

2-acetamido-9-D-ribofuranosyl-6-(2-(phenylthio)ethyl) purine (shown as compound (5) in FIG. 6) is produced by removing the tert-butyldimethylsilyl (TBDMS) protecting groups of compound (4) (in FIG. 6). 1.4 g (1.77 mmoles) of compound (4) (in FIG. 6) is dissolved in 10 mL THF, treated with 10 mL of a 1 M tetra-n-butylammonum fluoride (TBAF) solution in THF, and stirred at room temperature for 6 hours. The volatiles are evaporated and the product, 2-acetamido-9-D-ribofuranosyl-6-(2-(phenylthio)ethyl)purine, is purified by silica gel chromatography using methanol:chloroform (8%).

A dimethoxytrityl (DMT) protecting group is added at the 5' position of the ribose moiety to produce 2-acetamido-5'-O-DMT-9-D-ribofuranosyl-6-(2-(phenylthio)ethyl)purine (shown as (6) in FIG. 6). 2-acetamido-9-D-ribofuranosyl-6-(2-(phenylthio)ethyl)purine (compound (5) in FIG. 6; 0.75 g; 1.6 mmoles) is dissolved in anhydrous pyridine (16 mL) and treated with DMT-Cl (1.05 molar equivalents) with stirring at room temperature for 6 hours. Water (5 mL) is added and the solution stirred for additional 10 minutes. Volatiles are evaporated under reduced pressure and the residue dissolved in dichloromethane (75 mL) and washed twice with a saturated solution of sodium bicarbonate (2×50 mL), water (50 mL), and brine (50 mL). The organic residue is dried with magnesium sulfate, filtered, and evaporated under reduced pressure to yield 2-acetamido-5'-O-DMT-9-D-ribofuranosyl-6-(2-(phenylthio)ethyl)purine, which is used in the next step without purification.

2-acetamido-5'-O-DMT-9-D-ribofuranosyl-6-(2-(phenylthio)ethyl)purine is further modified by addition of a 2' (triisopropylsilyl)oxy]methyl group to produce 2-acetamido-5'-O-DMT-2'-O-TOM-9-D-ribofuranosyl-6-(2-(phenylthio) ethyl)purine (shown as (7) in FIG. 6). 2-acetamido-5'-O-DMT-9-D-ribofuranosyl-6-(2-(phenylthio)ethyl)purine (1.2 g, 1.6 mmoles) is dissolved in 1,2-dichloroethane (16 mL) and treated with t-Bu$_2$SnCl$_2$ (1.0 molar equivalents) and diisopropylethylamine (3.5 molar equivalents) and stirred at room temperature for 30 minutes. [(Triisopropylsilyl)oxy] methyl chloride (1.1 molar equivalents) is added to the solution and stirred for additional 30 minutes. Volatiles are evaporated under reduced pressure and the residue dissolved in dichloromethane (75 mL), washed twice with a saturated solution of sodium bicarbonate (2×50 mL), and washed once with brine (50 mL). The organics are dried with magnesium sulfate, filtered, and evaporated under reduced pressure. 2-acetamido-5'-O-DMT-2'-O-TOM-9-D-ribofuranosyl-6-(2-(phenylthio)ethyl)purine is isolated by column chromatography using hexane/ethyl acetate 9:1→1:1.

2-acetamido-5'-O-DMT-2'-O-TOM-3'-cyanoethyl diisopropylphospharamidite-9-D-ribofuranosyl-6-(2-(phenylthio)ethyl)purine ((1) in FIG. 6) is prepared by dissolving 0.6 g (0.6 mmoles) of 2-acetamido-5'-O-DMT-3'-O-TOM-9-D-ribofuranosyl-6-(2-(phenylthio)ethyl)purine in dichloromethane (6 mL), cooling in an ice bath, and treating with diisopropylethylamine (3 molar equivalents) and cyanoethyl diisopropyl-phosphoramidochloriditite (1.2 molar equivalents). The solution is stirred for 2 hours at room temperature. Dichloromethane (40 mL) is added and the solution is washed twice with 10% aqueous sodium bicarbonate (2×30 mL) and water (30 mL). The organics are dried with magnesium sulfate and the product is purified by column chromatography on silica using hexane/ethyl acetate 9:1→1:1. The desired product is obtained as an off-white foam.

Example 6

Synthesis of Oligonucleotides Containing 2-amino-6-vinylpurine

RNA oligonucleotides containing a 2-amino-6-vinyl purine moiety are synthesized via solid phase synthesis using TOM-protected RNA amidites (Glen Research; Sterling, Va.) and 2-acetamido-5'-O-DMT-2'-O-TOM-3'-cyanoethyl diisopropylphospharamidite-9-D-ribofuranosyl-6-(2-(phenylthio)ethyl)purine on an Expedite (Millipore; Billerica, Mass.) RNA synthesizer using the conditions recommended by the manufacturers.

After the synthesis, the oligonucleotides are cleaved from the solid support by treatment with ammonium hydroxide (30%, 12 hours) and dried using a vacuum centrifuge. The crude 2'-TOM protected RNA (1 µmol) is treated with a solution of magnesium monoperphthalate (MMPP; 2.9 µmoles) in carbonate buffer (10 mM, pH 10; 50 µL), followed by treatment with 10N sodium hydroxide (0.15 mL). The solution is neutralized with acetic acid and then evaporated to dryness. The 2'-TOM-protected 2-amino-6 vinyl purine containing oligonucleotide is dissolved in DMSO (100 µL) and treated with triethylamine (65 µL), followed by triethylammonium trihydrofluoride (75 µL), and incubated at 65° C. for 2 hours. FIG. 7 illustrates these steps. The deprotected RNA is precipitated with butanol, washed once with 100% cold ethanol and once with 70% ethanol/water.

The pellet is dissolved in 0.1 mL of diethylpyrocarbonate (DEPC)-treated water and purified by ion exchange HPLC on a Dionex (Sunnyvale, Calif.) DNA-pac column using a gradient of 0.01 M NaCl to 1 M NaCl containing EDTA in nuclease-free water. The major fraction is collected and desalted in an OPC purification cartridge (ABI; Carlsbad, Calif.) using the conditions recommended by the manufacturer.

The 2-amino-6 vinyl-modified oligonucleotide is ligated onto the end of an mRNA preparation containing the sequences of interest by splint ligation, in which the mRNA and activated oligonucleotide are annealed to a DNA oligonucleotide containing sequences complementary to both the mRNA and the activated oligonucleotide and are joined together using T4 DNA ligase (New England BioLabs, Ipswich, Mass.). The resulting mRNA is then subjected to in vitro translation and tRNA crosslinking.

Example 7

Synthesis of Linking tRNA Molecules Containing an Activated 4-thiouridine Residue A linking tRNA comprising an activated $^{4S}U$ moiety can be synthesized from an oligonucleotide prepared as described in Example 1. A first RNA oligonucleotide comprising the 5' portion of the tRNA (extending from the 5' end to the last base of the anticodon) is synthesized, wherein a $^{4S}U$ residue is incorporated at the desired position in the anticodon. The first oligonucleotide is annealed to a second RNA oligonucleotide, corresponding to the 3' portion of the tRNA, that begins with the first base 3' of the anticodon and extends to the base preceding the terminal A of the mature tRNA. The second RNA may be produced by chemical synthesis or by in vitro transcription of an appropriate DNA sequence. The first and second oligonucleotides are ligated together using T4 DNA ligase (New England BioLabs, Ipswich, Mass.). To facilitate ligation, a 20-nucleotide bridging or splint DNA that is complementary to 10 bases on each side of the junction is annealed to the two RNA oligonucleotides prior to ligation. The ligation product is denatured by heating and purified by polyacrylamide gel electrophoresis in the presence of 8 M urea. The synthesis of tRNA molecules from subfragments has been described (e.g., U.S. Pat. Nos. 6,962,781; 7,351,812; 7,410,761; and 7,488,600). 3'-Amino-3'-deoxyadensoine is prepared using known methods and attached to the ligation product purified above using tRNA nucleotidyl transferase (Fraser, T. H. and Rich, A., *Proc. Natl. Acad. Sci. U.S.A.* 70:2671-2675, 1973; Merryman, C. et al., (2002). *Chem, Biol.* 9:741-746, and references therein). Alternatively, a dinucleotide consisting of cytidine-3'-amino-3'-deoxyadenosine or a trinucleotide consisting of 5'-phospho-cytidine-cytidine-3'-amino-3'-deoxyadenosine can be chemically synthesized (Zhang, B., Zhang, L., Sun, L., Cui, Z. (2002) *Org. Lett.* 4:3615-3618, 2002) and used as a replacement of the corresponding terminal nucleotides of the mature tRNA via ligation with T4 RNA ligase. The resulting 3'-amino-terminated tRNA can be charged with an amino acid using the appropriate aminoacyl tRNA synthetase (Fraser, T. H. et al., op. cit.; Merryman, C. et al., op. cit.). Finally, the amidated tRNA is activated with N,N'-bis-bromoacetyl-1,2-diaminobenzene as described in Example 1. Alternatively, it is activated prior to or after ligation of the 5' and 3' tRNA fragments.

The 3' tRNA fragment can also be synthesized with puromycin replacing the 3' terminal adenosine using standard phosphoramidite methods (available from IDT, Coralville, Iowa). The resulting tRNA contains an amide-linked O-methyltyrosine at its 3' end.

Example 8

Synthesis of 3'-amino-5'-DMT-2'-TOM-N-6-Benzoyl-3'-deoxyadenosine

3'-Azido-3'-deoxyadenosine is synthesized as described by Robins et al. (*J. Org. Chem.* 66:8204-8210, 2001). 3'-azido-3'-deoxyguanosine (2.92 g; 10 mmol) is dissolved in anhydrous pyridine (60 mL) with vigorous stirring under an argon atmosphere and cooled on an ice bath, followed by treatment with trimethylsylil chloride (3 molar equivalents; mol eq), and stirring for 60 minutes at room temperature. The resulting solution containing the sylilated nucleoside is cooled on an ice bath and treated with benzoyl chloride (1.2 mol eq), allowed to reach room temperature, and then stirred for 4 hours. Water (10 mL) is added and the solution is stirred for 10 minutes. Concentrated ammonium hydroxide (20 mL) is added and the reaction mixture is stirred for 15 minutes at room temperature. The resulting mixture was then evaporated to dryness under reduced pressure. The dried residue is stirred with cold water, filtered, and dried under high vacuum with phosphorus pentoxide, yielding 3'-azido-6-N-benzoyl 3'-deoxyadenosine.

A dimethoxytrityl (DMT) protecting group is added at the 5' position of the ribose moiety to produce 3'-azido-5'-DMT-6-N-benzoyl-3'-deoxyadenosine. 3'-Azido-6-N-benzoyl 3'-deoxyadenosine (8 mmol) is dissolved in anhydrous pyridine (80 mL) and treated with DMT-Cl (1.1 mol eq) and stirred at room temperature for 6 hours. Water (5 mL) is added and the solution stirred for additional 10 minutes. Volatiles are evaporated under reduced pressure and the residue dissolved in dichloromethane (150 mL) and washed twice with a saturated solution of sodium bicarbonate (2×50 mL), water (50 mL), and brine (50 mL). The organic residue is dried with magnesium sulfate, filtered, and evaporated under reduced pressure. The obtained solid is crushed with ethyl ether and filtered to obtain 3'-azido-5'-DMT-6-N-benzoyl-3'-deoxyadenosine, which is used in the next step without purification.

3'-Azido-5'-DMT-6-N-benzoyl-3'-deoxyadenosine is further modified by addition of a 2' (triisopropylsilyl)oxy]methyl (TOM) group to produce 3'-azido-2'-TOM-5'-DMT-6-N-benzoyl-3'-deoxyadenosine.

3'-Azido-5'-DMT-6-N-benzoyl-3'-deoxyadenosine (7.8 mmol) is suspended in dichloroethane (100 mL) containing diisopropylethylamine (1.5 mol eq) and cooled on an ice bath. [(Triisopropylsilyl)oxy]methyl chloride (1.1 mol eq) is added to the solution and stirred for 60 minutes at room temperature, at which point water (2 mL) is added and stirred for 5 minutes. Volatiles are evaporated under reduced pressure and the residue dissolved in dichloromethane (150 mL), washed twice with a saturated solution of sodium bicarbonate (2×50 mL), and washed once with brine (50 mL). The organics are dried with magnesium sulfate, filtered, and evaporated under reduced pressure. The resulting solid is purified by column chromatography on silica gel using dichloromethane/methanol (97:3) as the mobile phase. Fractions containing the desired product are evaporated under reduced pressure.

The azido functionality in 3'-azido-2'-TOM-5'-DMT-6-N-benzoyl-3'-deoxyadenosine is reduced to an amine residue via catalytic hydrogenation with palladium 3'-azido-2'-TOM-5'-DMT-6-N-benzoyl-3'-deoxyadenosine (6 mmol) is dissolved in ethanol (120 mL) containing 10% Pd/C (0.6 mol eq) and treated with hydrogen gas (1 atm) for 12 hours. The solution is filtered through a pad of celite and the celite washed with ethanol (60 mL). The solvent is evaporated and the resulting white powder dried under high vacuum to yield 3'-amino-5'-DMT-2'-TBDMS-N-6-benzoyl-3'-deoxyadenosine.

Example 9

Solid Support Immobilization of 3'-amino-5'-DMT-2'-TBDMS-N-6-benzoyl-3'-deoxyadenosine The amino-containing nucleoside is covalently linked to a controlled pored glass solid phase synthesis support using the general procedure reported by Eisenhut and Richert, *J. Org. Chem.* 74:26-37, 2009.

Example 10

Solid Phase Synthesis of Amino-terminated Trinucleotide pCpCpA-3'-NH$_2$

Trinucleotide pCpCpA-3'-NH$_2$ is synthesized on a 5-micromole scale via solid phase synthesis on CPG-immobilized 3'-amino-5'-DMT-2'-TBDMS-N-6-benzoyl-3'-deoxyadenosine using standard phosphoramidite chemistry. The synthesis is performed on an Expedite (Millipore; Billerica, Mass.) RNA synthesizer using the conditions recommended by the manufacturers. After the synthesis, the trinucleotide is cleaved from the solid support by treatment with ammonium hydroxide (30%, 12 hours) and dried using a vacuum centrifuge. The 2'-TOM-protected trinucleotide is dissolved in DMSO (100 µL) and treated with triethylamine (65 µL), followed by tributylammonium trihydrofluoride (75 µL), and incubated at 65° C. for 6 hours. The sample is diluted in water (20 mL), lyophilized, and purified by preparative HPLC on a C$_{18}$ reverse phase column using a linear gradient of 0-30% methanol in triethylammonium bicarbonate (10 mM). Fractions containing the desired product are lyophilized to dryness.

The 3'-amino modified trinucleotide is ligated onto the end of an mRNA preparation containing the sequences of interest by splint ligation, in which the mRNA and activated oligo are annealed to a DNA oligonucleotide containing sequences complementary to both the mRNA and the activated oligonucleotide, and joined together using T4 DNA ligase (New England BioLabs, Ipswich, Mass.).

Example 11

Preparation of Azido-modified Oligonucleotides from 3'-amino 3'-deoxyadenosine-containing Oligonucleotides An oligonucleotide (5 micromoles) containing a single terminal 3'-amino nucleoside as described in Example 10 is dissolved in 50 µL of 70 mM boric acid (pH 8.5) and cooled on an ice-bath. Formamide (30 µL) is added, followed by addition of a freshly prepared solution of N-(5-azido-2-nitrobenzoyloxy)succinimide (15 molar equivalents) (Sigma-Aldrich, St. Louis, Mo.) in DMF (40 µL) (Handbook of RNA Biochemistry; Hartmann, R. K., Bindereif, A., Schon, A., and Westhof, E. M., Eds., 2005, Wiley-VCH). The resulting solution is incubated for 60 minutes on ice and a second aliquot of the NHS-azido ester is added and incubated for an additional hour. The solution is extracted twice with chloroform (300 µL) at room temperature and precipitated by addition of 20 µL of 3 M sodium acetate and 1.3 mL ethanol. The mixture is cooled to −70° C. for 1 hour and the precipitated oligonucleotide pelleted by centrifugation. The oligonucleotide is washed once with 70% ethanol, centrifuged, and evaporated to dryness using a Speed-Vac lyophilizer. The oligonucleotide is purified by preparative reverse phase HPLC on a C-18 column using a linear gradient of triethylammonium acetate (20 mM) to 60% acetonitrile in triethylammonium acetate (20 mM). Fractions containing the oligonucleotide are lyophilized to dryness. The resulting mRNA is then subjected to in vitro translation reaction and crosslinked to its peptide target by either one of the two procedures described below.

Example 12

Photocrosslinking of Azido-containing mRNA and an Amino Acid Side Chain at the Peptidyl Transfer Center An mRNA containing a single terminal azido modification is subjected to an in vitro translation reaction and crosslinked to its peptide target by irradiation with UV light using a Rayonet RPR100 photoreactor at 4° C. for 2 hours. Crosslinked peptide-mRNA fusions are isolated by treating the translation mixture with a release buffer (1M NaCl, 20 mM EDTA, 0.1 Bicine, pH 8.3) and then by oligonucleotide affinity purification on an oligo-dT containing column.

Example 13

Crosslinking of Azido-containing mRNA and an Alkyne-containing Amino Acid Side Chain at the Peptidyl Transfer Center Via Copper-catalyzed Huisgen Cycloaddition An mRNA containing a single terminal azido modification is subjected to an in vitro translation reaction and crosslinked to its peptide target, which contains an amino acid with an alkynyl side chain at the peptidyl transfer center, by addition of a Cu(I) containing salt and incubation at 4° C. for 10 hours (Neumann, H. et al., *Nature*, 464, 441-444, 2010). Crosslinked peptide-mRNA fusions are isolated by treating the translation mixture with a release buffer (1M NaCl, 20 mM EDTA, 0.1 Bicine, pH 8.3) and then by oligonucleotide affinity purification on an oligo-dT containing column.

What is claimed is:

1. A method for linking an mRNA molecule to a polypeptide, the method comprising:
   (a) providing an mRNA molecule comprising a nucleophilic nucleoside partner;
   (b) providing a translation system comprising a linking aminoacyl-tRNA comprising an amino acid residue linked to a linking tRNA by a covalent bond, wherein the linking tRNA comprises an anticodon comprising a crosslinker, wherein the crosslinker is an electrophilic nucleoside that reacts with a nucleophilic nucleoside partner via hybridization-triggered alkylation;
   (c) translating the mRNA molecule in the translation system to produce a polypeptide into which the amino acid residue, still linked to the linking tRNA, is incorporated; and
   (d) during or after step (c), crosslinking the crosslinker of the linking tRNA to the nucleophilic nucleoside partner of the mRNA molecule, thereby linking the mRNA molecule to the polypeptide through the linking tRNA, wherein the electrophilic nucleoside and the nucleophilic nucleoside partner are selected from the group consisting of:
   (i) 2-amino-6-vinylpurine and cytosine;
   (ii) 2-amino-6-vinylpurine and 4-thiouridine;
   (iii) 2-alpha-halomethyl adenosine and 2-thiouridine;
   (iv) 8-alpha-halomethyl purine and 4-thiouridine;
   (v) 2,8-alpha-halomethyl purine and 4-thiouridine;
   (vi) 5-methyl-N4,N4-ethanocytosine and cytosine;
   (vii) 2-amino-6-(1-ethylsulfinyl)vinyl purine nucleoside and cytosine;
   (viii) 4-amino-6-oxo-2-vinylpyrimidine nucleoside and uridine; and
   (ix) 4-amino-6-oxo-2-vinylpyrimidine-ethyl-C-nucleoside and uridine.

2. The method of claim 1, wherein the translation system is a purified in vitro translation system.

3. The method of claim 1, wherein the electrophilic nucleoside and its nucleophilic nucleoside partner are 2-amino-6vinylpurine and cytosine, respectively.

* * * * *